(12) United States Patent
Lee et al.

(10) Patent No.: US 7,271,260 B2
(45) Date of Patent: Sep. 18, 2007

(54) 3,4-DIHYDROQUINAZOLINE DERIVATIVES AS T-TYPE CALCIUM CHANNEL BLOCKERS AND METHOD OF PREPARING THE SAME

(75) Inventors: Yong Sup Lee, Seoul (KR); Jae Yeol Lee, Seoul (KR); Hyewhon Rhim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 76 days.

(21) Appl. No.: 11/018,786

(22) Filed: Dec. 20, 2004

(65) Prior Publication Data

US 2005/0197351 A1   Sep. 8, 2005

(30) Foreign Application Priority Data

Feb. 24, 2004 (KR) ............... 10-2004-0012144

(51) Int. Cl.
*C07D 239/84* (2006.01)
*C07D 239/74* (2006.01)
*A61K 31/517* (2006.01)
*A61K 31/5377* (2006.01)

(52) U.S. Cl. .................. 544/119; 544/283; 514/266.1; 514/266.2; 514/266.22; 514/252.17; 514/234.5

(58) Field of Classification Search ............ 514/266.1, 514/266.2, 266.22; 544/283, 284, 119
See application file for complete search history.

(56) References Cited

FOREIGN PATENT DOCUMENTS

WO    WO 03007953 A    1/2003
WO    WO 03031415 A    4/2003

OTHER PUBLICATIONS

Takao Saito et al: "A Facile and Efficient Carbodiimide-Mediated Synthesis of Dihydroquinazolines via a Tandem Nucleophilic Addition-Intramolecular Hetero Conjugate Addition Annulation Strategy" Tetrahedron Letters, Elsevier Science Publishers, Amsterdam, NL, vol. 37, No. 2, 1996, pp. 209-212, XP002326650.
Wang F et al: "Solid-Phase Synthesis of 3,4-Dihydroquinazoline" Tetrahedron Letters, Elsevier Science Publishers, Amsterdam, NL, vol. 38, No. 50, (Dec. 15, 1997), pp. 8651-8654, XP004097142.
S. I. Ertel et al: "Mibefradfil (Ro 40-5967): the first selective T-type Ca2+ channel blocker" Expert Opinion on Investigational Drugs, vol. 6, No. 5, 1997, pp. 569-582 XP002332318.
Yong Sup Lee et al: "3,4-Dihydroquinazoline derivatives as novel selective T-type Ca2+ channel blockers" Bioorganic & Medicinal Chemistry Letters, Oxford, GB, vol. 14, 2004, pp. 3379-3384, XP002326652.
Munikumar Reddy Doddareddy et al: "First pharmacophoric hypothesis for T-type calcium channel blockers" Bioorganic & Medicinal Chemistry, vol. 12, 2004, pp. 1605-1611, XP002332319.

*Primary Examiner*—Emily Bernhardt
*Assistant Examiner*—Tamthom N. Truong
(74) *Attorney, Agent, or Firm*—Jones Day

(57) ABSTRACT

The present invention relates to 3,4-dihydroquinazoline derivatives as T-type calcium channel blockers and a method of preparing the same. The present invention further relates to a composition comprising the same. The composition comprising the 3,4-dihydroquinazoline derivatives of the present invention can be effectively used for preventing and treating angina pectoris, high blood pressure, myocardial disease, pain and epilepsy by blocking the T-type calcium channel.

3 Claims, 3 Drawing Sheets

(1) KYS00294; (2) KYS00409; (3) KYS00503; (4) KYS05000; (5) KYS05001; (6) KYS05020; (7) KYS05020A; (8) KYS05050B; (9) KYS05050C (1) KYS00503; (2) KYS05000; (3) KYS05001

3,4-DIHYDROQUINAZOLINE DERIVATIVES AS T-TYPE CALCIUM CHANNEL BLOCKERS AND METHOD OF PREPARING THE SAME

FIELD OF THE INVENTION

The present invention relates to 3,4-dihydroquinazoline derivatives or a salt thereof as T-type calcium channel blockers and a method of preparing the same. The present invention further relates to a composition comprising the same for blocking the T-type calcium channel.

BACKGROUND OF THE INVENTION

Calcium in nerve cells plays an important role in transferring signals between the nerve cells. There are several channels for calcium. However, when a terminal stimulus is transferred thereto, a voltage-dependent $Ca^{2+}$ channel works primarily. That is, the voltage-dependent $Ca^{2+}$ channel as a membrane protein regulates various intracellular functions (e.g., muscle contraction, neurogenesis, synapse plasticity, secretion of neurotransmitter and hormone, gene expression, etc.) by controlling an inflow of calcium ion from a cell exterior.

The voltage-dependent $Ca^{2+}$ channel can be functionally classified into two groups depending on its biophysical property: a low voltage-activated $Ca^{2+}$ channel (hereinafter referred to as "LVA"), which is activated at lower voltage; and a high voltage-activated $Ca^{2+}$ channel (hereinafter referred to as "HVA"), which is activated at higher voltage. The HVA calcium channel is subdivided into L-, P/Q-, N- and R-types depending on a pharmacological property of the current induced thereby The LVA calcium channel is characterized by small conductivity being very quickly activated and inactivated. Thus, it belongs to T (transient)-type calcium channel (Tsien, R. W. et al., *Trends Neurosci.* 1988, 11, 431-438).

It has been reported that the T-type calcium channel is involved in bursting firing of nerve cells (Huguenard, J. R. et al., *Annu. Rev. Physiol.* 1996, 58, 329-348), pacemaker activity of the heart (Zhou, Z. et al., *J. Mol. Cell. Cardiol.* 1994, 26, 1211-1219), secretion of aldosterone (Rossier, M. F. et al., *Endocrinology* 1996, 137, 4817-4826), fertilization (Arnoult, C. et al., *Proc. Natl. Acad. Sci.* 1996, 93, 13004-13009) and pain relief (Ikeda, H. et al., *Science* 2003, 299, 1237-1240).

The T-type calcium channel may become over-expressed due to genetic or environmental causes, such as epilepsy (Tsakiridou, E. et al., *J. Neurosci.* 1995, 15, 3110-3117), high blood pressure (Self, D. A. et al., *J. Vacs. Res.* 1994, 31, 359-366), ventricular hypertrophy (Nuss, H. B. et al., *Circ. Res.* 1995, 73, 777-7825), pain (Shin, H. S. et al., *Science* 2003, 302, 117-119), and angina pectoris (Van der Vring, J. A. et al., *Am. J. Ther.* 1999, 6, 229-233). It has been found that there are three types of genes, $\alpha_{1G}$, $\alpha_{1H}$ and $\alpha_{1I}$, in the T-type calcium channel through gene cloning techniques (Talley, E. M. et al., *J. Neurosci.* 1999, 19, 1895-1911). There have been numerous attempts to develop a blocking agent, which selectively inhibits the T-type calcium channel. However, there were no effective T-type calcium channel blockers except for Mibefradil and ZD7288 (Felix, R. et al., *Biochem. Biophys. Res. Commun.* 2003, 311, 187-192). Accordingly, by developing a selective T-type calcium channel blocker, it may be possible to develop an epochal treating agent for epilepsy, high blood pressure and pain-related diseases.

A representative drug for blocking the T-type calcium channel is Mibefradil of Hoffman La Roche Ltd. (registered trademark: Posicor). The drug was found to be effective in treating high blood pressure, angina pectoris and cerebral apoplexy. It has been placed in the market as a treating agent for high blood pressure since May of 1997. However, a side effect caused by a drug-drug interaction due to inhibition of CYP 3A4 hepatic enzyme was discovered. As such, the drug was withdrawn from the market on June of 1999, which was just 13 months from first entering the market.

Accordingly, there has been a need in the art to develop a selective T-type calcium channel blocker, which has a new structure that can substitute Mibefradil.

SUMMARY OF THE INVENTION

The object of the present invention is to provide a T-type calcium channel blocker having a new structural backbone, which shows therapeutic effects superior to Mibefradil without causing any side effects.

Specifically, the present invention provides novel 3,4-dihydroquinazole derivatives of Formula 1 or a salt thereof, which can be effectively used as selective T-type calcium channel blockers, and a method of preparing the same. Further, the present invention provides a composition comprising the same and a pharmaceutically acceptable carrier for blocking the T-type calcium channel. Furthermore, the present invention provides a method of treating a disorder selected from the group consisting of angina pectoris, high blood pressure, myocardial disease, pain and epilepsy by administering a therapeutically effective amount of a 3,4-dihydroquinazoline derivative or a pharmaceutically acceptable salt thereof <Formula 1>

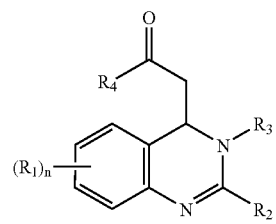

wherein, n is an integer ranging from 1 to 4;

$R_1$ is;

$R_2$ is $C_1$-$C_6$ alkyl, phenyl; morpholinyl; piperazinyl having a $C_1$-$C_4$ alkyl substituent at the $4^{th}$ position; 1-pyrrolidinyl; 1-piperidinyl; or —$NR_6R_7$, wherein $R_6$ and $R_7$ are each independently $C_1$-$C_6$ alkyl;

$R_3$ is $C_1$-$C_6$ alkyl or phenyl;

$R_4$ is

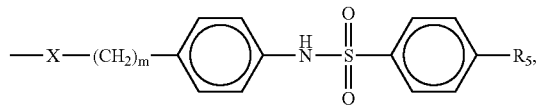

wherein X is O or NH; m is an integer ranging from 1 to 4; and $R_5$ is $C_1$-$C_4$ alkyl or halogen.

DETAILED DESCRIPTION OF THE PREFERRED EMBODIMENTS

Figure 1:
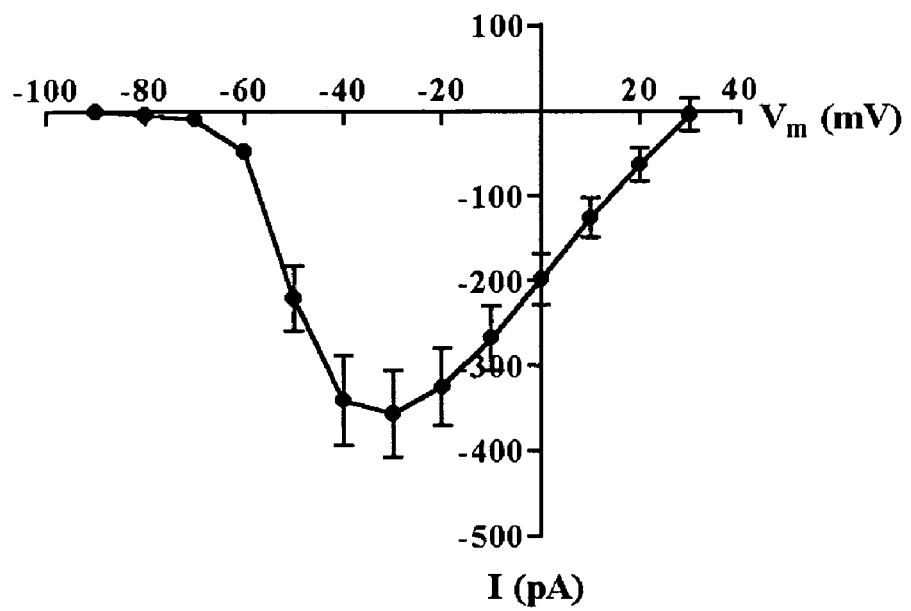
FIG. 1 is a graph showing the property of T-type calcium channel, which is activated mostly at a low voltage of −30 mV.

The present disclosure is based on investigations of 3,4-dihydroquinazole deriatives, which are effective for selectively blocking the T-type calcium channel.

Representative examples of the preferred compounds of Formula 1 of the present invention are:

4-(N-benzylacetamido)-3-phenyl-2-(piperidine-1-yl)-3,4-dihydroquinazoline (KYS05001), 4-(N-benzylacetamido)-3-phenyl-2-(morpholin-1-yl)-3,4-dihydroquinazoline (KYS05026), 4-(N-benzylacetamido)-3-phenyl-2-(4-methylpiperazinyl)-3,4-dihydroquinazoline (KYS05028), 4-[N-(4-nitrobenzyl)acetamido]-3-phenyl-2-(piperidine-1-yl)-3,4-dihydroquinazoline (KYS05034)

4-{N-[4-(4-methylbenzenesulfonylamido)benzyl]acetamido}-3-phenyl-2-(piperidine-1-yl)-3,4-dihydroquinazoline (KYS05041), and 4-{N-[4-(4-fluorobenzenesulfonylamido)benzyl]acetamido}-3-phenyl-2-(piperidine-1-yl)-3,4-dihydroquinazoline (KYS05042). The respective formulas of the compounds described above are as follows:

KYS05001
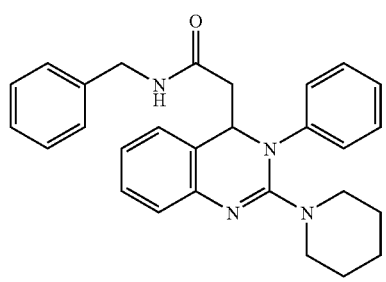

KYS05026
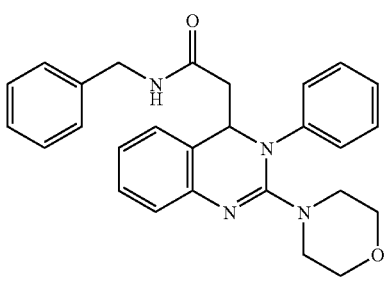

KYS05028
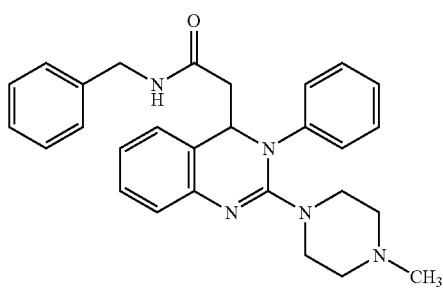

KYS05034
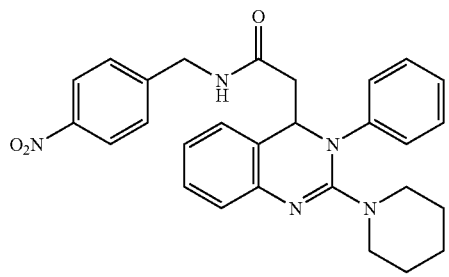

KYS05041
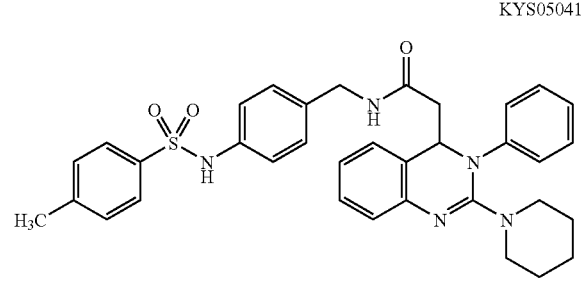

KYS05042
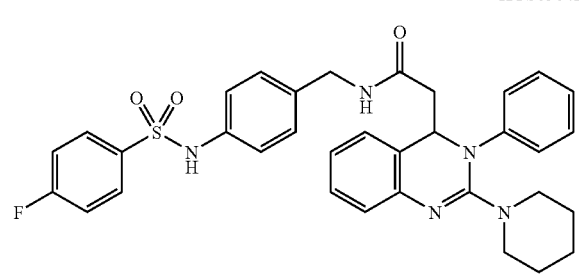

The compound of the present invention may be prepared by such processes as shown in the Reaction Schemes 1 and 2, which are given for the purposes of illustration only and are not intended to limit the scope of the present invention.

<Reaction Scheme 1>

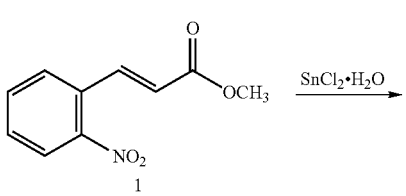

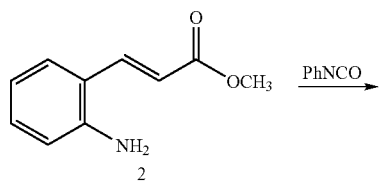

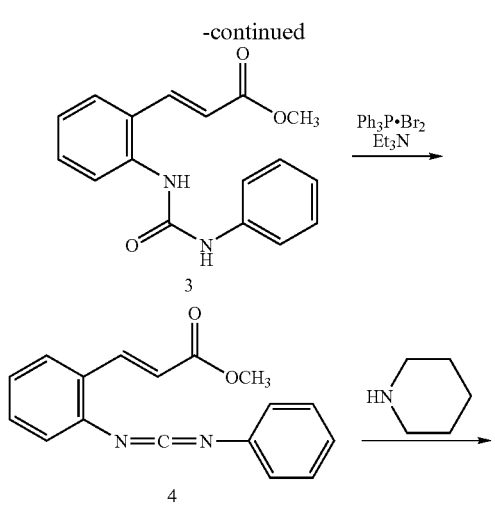

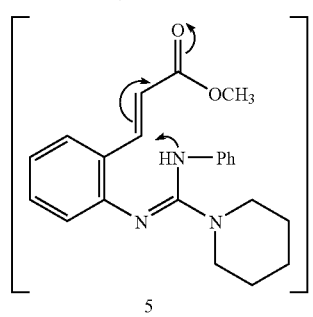

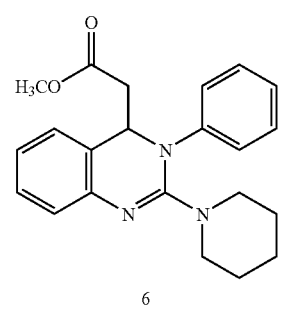

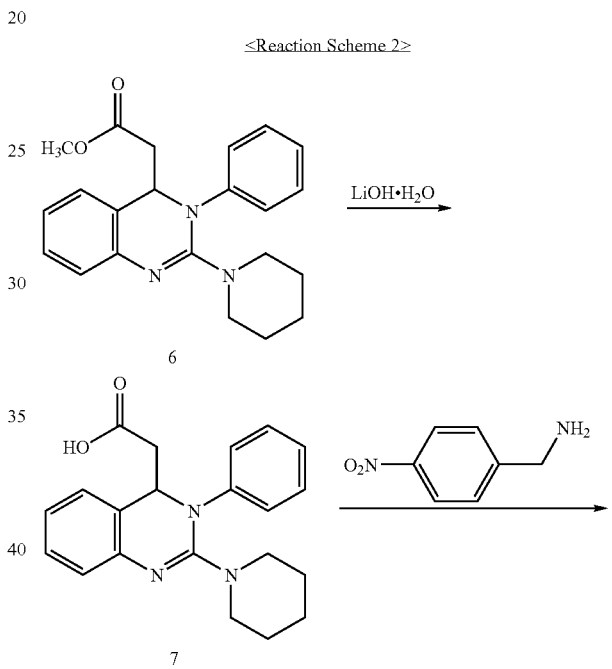

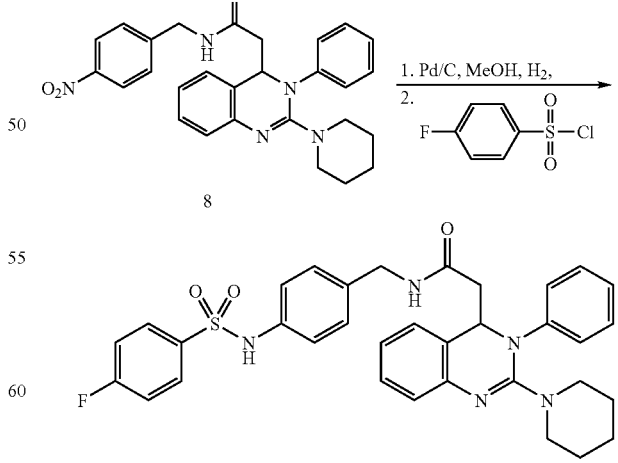

a urea-type compound (3). The urea-type compound is subjected to dehydration reaction using dibromotriphenylphosphine and triethylamine to obtain the carbodiimide compound (4) (Gololobov, Y G. et al., *Tetrahedron* 1992, 48, 1353-1406; Larksarp, C. et al., *J. Org. Chem.* 1998, 63, 6229-6233). In this step, if phenylisocyanate is replaced by isocyanate or tioisocyanate, it is capable of incorporating various substituents at the third position of dihydroquinazoline.

When the carbodiimide compound (4) reacts with various heteroatomic nucleophils such as alcohol, thioalcohol and amine (preferably piperidine in Reaction Scheme 1) under the presence of a solvent (e.g., benzene), the heteroatom carries out nucleophil adding reaction to a central carbon of the carbodiimide group. The compound (5) is subjected to intermolecular sequential 1,4-addition reaction in order to obtain 3,4-dihydroquinazoline (6) as an intermediate of the compound of the present invention.

A carbodiimide compound (4) as an intermediate of the compound of the present invention can be synthesized according to a conventional method described by Wang, F., et al. (*Tetrahedron Lett.* 1997, 38, 8651-8654) if properly modified. In a preferred embodiment of the present invention, methyl 2-nitrocinnamate (1) as a starting material is treated with SnCl₂ at an appropriate temperature (preferably 70° C.) to reduce a nitro group into an amine group. Generally, the carbodiimide is prepared through aza-Wittig reaction between iminophosphoranes and hetero-cumulenes (isocyanate or tioisocyanate) (Wamhoff, H. et al., *Adv. Heterocycl. Chem.* 1995, 64, 159; Molina, P. et al., *Synthesis* 1994, 1197-1217). However, the preparation of a urea-type compound, rather than that of the iminophosphorane having three phenyl rings, gives quantitative yield rate at a room temperature. Thus, its reaction condition is simpler. As such, the present invention employs a method of synthesizing the carbodiimide from a urea-type compound.

Accordingly, an amine compound (2) thus obtained is dissolved in tetrahydrofuran (THF) or benzene (preferably benzene), in which phenylisocinate is added thereto. Then, the mixture is stirred at a room temperature in order to obtain A methyl ester group of the intermediate compound (6) of the present invention is hydrolyzed into lithium hydroxide in a solvent mixture of THF and water at a proper temperature (preferably 60° C.) to obtain a free carboxylic compound (7) quantitatively. The free carboxylic compound (7) is subjected to a coupling reaction with various alcohol and amine (preferably nitrobenzylamine in Reaction Scheme 2) by using 1-[3-(dimethylamine)propyl]-3-ethylcarbodiimide hydrochloric acid (EDC) and 1-hydroxybenzotriazole (HOBT) in order to obtain an amido compound (8) (Gaucher, A. et al., *Tetrahedron: Asymmetry* 2001, 12, 2571-2580; Dhaon, M. K. et al., *J. Org. Chem.* 1982, 47, 1962-1965). The amido compound (8) is subjected to hydrogenation to reduce its nitro group into an amino group under the presence of methanol as a solvent and palladium (Pd) as a catalyst. This is to obtain an amine compound (9). The amine compound (9) is subjected to a coupling reaction with various sulfonylhalide (preferably 4-fluorobenzenesulfonyl chloride in Reaction Scheme 2) to obtain a sulfonamido compound (10), which is the final compound of the present invention.

The present invention will now be described in detail with reference to the following examples, which are not intended to limit the scope of the present invention.

EXAMPLE 1

Preparation of methyl 2-aminocinnamate (2)

Methyl 2-nitrocinnamate (1) (0.202 g, 0.975 mmol) was dissolved in 20 ml of ethyl acetate and $SnCl_2 \cdot 2H_2O$ (1.11 g, 4.87 mmol) was added thereto. The reaction mixture was heated at 70° C. for 1 hour. After the reaction was completed, the reaction mixture was cooled to a room temperature. The reaction mixture was adjusted to a weak alkaline solution with a saturated sodium bicarbonate solution and then filtered with fine clay layer (Celite 545). A water layer was extracted with ethyl acetate three times, in which an organic layer collected therefrom was dried with anhydrous magnesium sulfate. Thereafter, the solvent was removed under reduced pressure. The reaction mixture was subjected to column chromatography (hexane:ethyl acetate=5:1) to purify the title compound (2) in the form of a yellow crystal (0.161 g, 93%) (mp 67° C.).

IR (KBr) 3365, 2364, 1704, 1622, 1330, 1198, 756 cm$^{-1}$; $^1$H NMR (300 MHz, CDCl$_3$) δ 7.86 (d, J=15.9 Hz, 1H, —CH=CH—O$_2$Me), 7.40 (d, J=7.5 Hz, 1H, aromatic), 7.19 (t, J=7.2 Hz, 1H, aromatic), 6.78 (t, J=7.8 Hz, 1H, aromatic), 6.72 (d, J=7.5 Hz, 1H, aromatic), 6.38 (d, J=15.9 Hz, 1H, —CH=CH—CO$_2$Me) 4.02 (br, 2H, —NH$_2$), 3.82 (s, 3H, —OCH$_3$); $^{13}$C NMR (75 MHz, CDCl$_3$) δ 168.0, 145.9, 140.6, 131.6, 128.3, 120.1, 119.2, 117.9, 117.0, 51.9.

EXAMPLE 2

Preparation of methyl 3-[2-(3-phenylureido)phenyl]acrylate (3)

Methyl 2-aminocinnamate (2) (6.35 g, 35.8 mmol) was dissolved in 150 ml of benzene and phenylisocyanate (5.12 g, 43.0 mmol) was slowly dropped thereto at a room temperature. The reaction mixture was stirred for 12 hours to obtain a solid precipitate. Then, the precipitate was washed with ether in order to obtain the title compound (3) in the form of a white crystal (10.2 g, 96%) (mp 184° C.).

IR (KBr) 3346, 3278, 1724, 1650, 1548, 1322, 1172, 758, 672 cm$^{-1}$; $^1$H NMR (300 MHz, DMSO) δ 8.94 (s, 1H, —NH—CO—) 8.49 (s, 1H, —NH—CO—) 7.89 (d, J=15.9 Hz, 1H, —CH=CH—CO$_2$Me), 7.76 (d, J=7.8 Hz, 2H, aromatic), 7.46 (d, J=8.4 Hz, 2H, aromatic) 7.39 (t, J=8.1 Hz, 1H, aromatic), 7.28 (t, J=7.8 Hz, 2H, aromatic) 7.12 (t, J=7.5 Hz, 1H, aromatic) 6.97 (t, J=7.8 Hz, 1H, aromatic), 6.58 (d, J=15.3 Hz, 1H, —CH=CH—CO$_2$Me), 3.73 (s, 3H, —OCH$_3$); $^{13}$C NMR (75 MHz, DMSO) δ 167.4, 153.5, 140.5, 140.3, 138.5, 131.4, 129.5, 127.8, 126.8, 124.6, 124.4, 122.7, 119.5, 118.9, 52.2.

EXAMPLE 3

Preparation of methyl 3-[2-(phenyliminomethyleneamino)phenyl]acrylate (4)

The compound (3) (6.04 g, 20.4 mmol) and triethylamine (6.19 g, 61.2 mmol) were dissolved in 30 ml of dichloromethane and dibromotriphenyl-phosphine (12.9 g, 30.6 mmol) was gently added thereto at 0° C. The reaction mixture was stirred for 1 hour and extracted with dichloromethane three times. An organic layer collected therefrom was dried with anhydrous sodium sulfate and the solvent was removed under reduced pressure. The reaction mixture was subjected to column chromatography (hexane:ethyl acetate=20:1) to purify the title compound (4) in the form of a white crystal, carbodjimide (4), (4.26 g, 75%) (mp 54° C.).

IR (KBr) 2142, 1716, 1484, 1172, 756, 59 cm$^{-1}$; $^1$H NMR (300 MHz, CDCl$_3$) δ 8.18 (d, J=16.2 Hz, 1H, —CH=CH—CO$_2$Me), 7.56 (d, J=7.8 Hz, 1H, aromatic), 7.36-7.29 (m, 3H, aromatic), 7.25 (d, J=7.8 Hz, 1H, aromatic), 7.20-7.13 (m, 4H, aromatic), 6.52 (d, J=16.2 Hz, 1H, —CH=CH—CO$_2$Me), 3.80 (s, 3H, —OCH$_3$); $^{13}$C NMR (75 MHz, CDCl$_3$) δ 167.5, 140.5, 138.4, 138.0, 134.3, 131.3, 129.8, 129.0, 127.8, 126.1, 126.0, 125.9, 124.6, 119.6, 52.0.

EXAMPLE 4

Preparation of 4-methoxycarbonylmethyl-2-(1-piperidinyl)-3-phenyl-3,4-dihydroquinazoline (6)

The compound (4) (0.605 g, 2.17 mmol) was dissolved in 20 ml of benzene and piperidine (0.222 g, 2.60 mmol) was gently dropped thereto at a room temperature. The reaction mixture was stirred for 2 hours. After 2 hours, the reaction mixture was washed with water and brine. An organic layer was dried with anhydrous magnesium sulfate and the solvent was removed under reduced pressure. The reaction mixture was subjected to column chromatography (CH$_2$Cl$_2$: MeOH=10:1) to purify the title compound (6) in the form of a white crystal (0.632 g, 80%) (mp 109° C.).

$^1$H NMR (300 MHz, CDCl$_3$) δ 7.28-7.17 (m, 4H, aromatic), 7.09-7.01 (m, 3H, aromatic), 6.97-6.89 (m, 2H, aromatic), 5.10 (dd, J=4.5 and 10.8 Hz, 1H, —CH$_2$—CH—N—), 3.79 (s, 3H, —OCH$_3$), 3.42 (s, 4H, piperidinyl), 2.85 (dd, J=10.8 and 15.3 Hz, 1H, —CO—CH$_2$—), 2.52 (dd, J=4.7 and 15.5 Hz, 1H, —CO—CH$_2$—), 1.55-1.50 (m, 2H, piperidinyl), 1.43-1.40 (m, 4H, piperidinyl); $^{13}$C NMR (75 MHz, CDCl$_3$) δ 172.2, 153.2, 146.3, 144.4, 129.4, 128.6, 126.1, 124.9, 124.1, 123.1, 122.6, 122.4, 61.2, 52.0, 47.0, 39.8, 25.7, 25.0; HRMS (FAB, M+H) Calcd for C$_{22}$H$_{26}$N$_3$O$_2$ 364.2025, found 364.2019.

EXAMPLE 5

Preparation of 4-carboxy-2-(1-piperidinyl)-3-phenyl-3,4-dihydroquinazoline (7)

The compound (6) (0.235 g, 0.645 mmol) was dissolved in 10 ml of THF/water (1:1) and a hydrate of lithium hydroxide (0.135 g, 3.23 mmol) was added thereto at a room temperature. The reaction mixture was stirred at 60° C. for 2 hours. After the reaction was completed, the pH of the reaction mixture was adjusted to 3~4 and the reaction mixture was extracted with dichloromethane three times. An organic layer was dried with anhydrous magnesium sulfate and the solvent was removed under reduced pressure to quantitatively obtain the title compound in the form of a white crystal (7) (mp 238° C.).

$^1$H NMR (300 MHz, DMSO) δ 7.57 (d, J=7.8 Hz, 1H, aromatic), 7.45-7.26 (m, 7H, aromatic), 7.19 (m, 1H, aromatic), 5.29 (dd, J=6.3 and 9.3 Hz, 1H, —CH$_2$—C$\underline{H}$—N—), 3.36 (s, 4H, piperidinyl), 2.88 (dd, J=9.3 and 15.0 Hz, 1H, —CO—CH$_2$—), 2.69 (dd, J=6.3 and 15.1 Hz, 1H, —CO—CH$_2$—), 1.46-1.23 (m, 6H, piperidinyl); $^{13}$C NMR (75 MHz, CD$_3$OD) δ 174.6, 153.1, 143.7, 132.7, 130.1, 129.1, 127.5, 127.3, 126.3, 125.7, 124.7, 118.0, 62.8, 49.5, 42.6, 24.6, 23.3.

EXAMPLE 6

Preparation of 4-[N-(4-nitrobenzyl)acetamido]-2-(1-piperidinyl)-3-phenyl-3,4-dihydroquinazoline (8)

The compound (7) (0.22 g, 0.63 mmol) and 1-hydroxybenzotriazol (HOBT) (0.13 g, 0.94 mmol) were dissolved in 20 ml of dichloromethane/THF (1:1) and 4-nitrobenzylamine (0.18 mg, 0.94 mmol) was dropped thereto at 0° C. The reaction mixture was stirred at the same temperature for 1 hour. Then, 1-[3-(dimethylamine)propyl]-3-ethylcarbodiimide hydrochloric acid (EDC) (0.14 g, 0.75 mmol) was added to the reaction mixture and further stirred for 12 hours. After the reaction was completed, the solvent was removed under reduced pressure and the resulting solution was dissolved in dichloromethane. The reaction mixture was sequentially extracted with 0.5 M hydrochloric acid aqueous solution twice. Then, it was saturated with NaHCO$_3$ aqueous solution twice and water once and thereafter washed with brine. An organic layer was dried with anhydrous magnesium sulfate and the solvent was removed under reduced pressure. The reaction mixture was subjected to column chromatography (CH$_2$Cl$_2$:MeOH=10:1) to purify the title compound in the form of a white crystal (8) (0.24 g, 80%).

IR (KBr) 3192, 2932, 2848, 1668, 1552, 1486, 1430, 1344, 1282, 756 cm$^{-1}$; $^1$H NMR (300 MHz, CDCl$_3$) δ 8.58 (br, 1H, —CO—N$\underline{H}$—CH$_2$—), 8.15 (d, J=8.7 Hz, 2H, —CH$_2$—C$_4$$\underline{H}_4$—NO$_2$), 7.49 (d, J=8.1 Hz, 2H, —CH$_2$—C$_4$$\underline{H}_4$—NO$_2$), 7.27-7.20 (m, 2H, aromatic), 7.15-7.02 (m, 4H, aromatic), 6.95-6.87 (m, 3H, aromatic), 5.23 (dd, J=6.0 and 8.7 Hz, 1H, —CH$_2$—C$\underline{H}$—N—), 4.67 (dd, J=6.7 and 12.1 Hz, 1H, —NH—C$\underline{H}_2$—), 4.58 (dd, J=5.7 Hz and 15.3 Hz, 1H, —NH—C$\underline{H}_2$—), 3.10 (br, 4H, piperidinyl), 2.58 (dd, J=9.0 and 14.7 Hz, 1H, —CO—C$\underline{H}_2$), 2.32 (dd, J=6.1 and 14.2 Hz, 1H, —CO—C$\underline{H}_2$—), 1.35 (br, 2H, piperidinyl), 1.13 (br, 4H, piperidinyl); $^{13}$C NMR (75 MHz, CDCl$_3$) δ 170.9, 154.3, 147.4, 146.5, 145.9, 143.1, 129.5, 129.0, 128.5, 127.0, 125.4, 124.7, 124.0, 123.1, 123.0, 122.0, 60.8, 47.5, 43.2, 41.6, 25.2, 24.6; HRMS (FAB, M+H) Calcd for C$_{28}$H$_{30}$N$_5$O$_3$ 484.2349, found 484.2341.

EXAMPLE 7

Preparation of 4-[N-(4-aminobenzyl)acetamido]-2-(1-piperidinyl)-3-phenyl-3,4-dihydroquinazoline (9)

The compound (8) (1.39 g, 2.87 mmol) and 10% Pd(C) (0.28 g) were dissolved in 40 ml of methanol and stirred for 2 hours under hydrogen atmosphere. After the reaction was completed, the reaction mixture was filtered with Celite 545 and the solvent was removed therefrom under reduced pressure. The reaction mixture was subjected to column chromatography (CH$_2$Cl$_2$:MeOH=10:1) to purify an amine compound (1.26 g, 97%).

IR (KBr) 3218, 2930, 2850, 1648, 1550, 1480, 1430, 1350, 1282, 732 cm$^{-1}$; $^1$H NMR (300 MHz, CDCl$_3$) δ 7.26-7.22 (m, 2H, aromatic), 7.20-7.11 (m, 4H, aromatic), 7.07-7.02 (m, 3H, aromatic), 6.96-6.90 (m, 2H, aromatic), 6.60-6.56 (m, 2H, aromatic), 6.37 (br, 1H, —CO—N$\underline{H}$—CH$_2$—), 5.17 (dd, J=5.1 and 9.6 Hz, 1H, —CH$_2$—C$\underline{H}$—N—), 4.32 (d, J=5.7 Hz, 2H, —NH—C$\underline{H}_2$—), 3.51 (br, 2H, —C$_4$H$_4$—N$\underline{H}_2$), 3.26 (br, 4H, piperidinyl), 2.57 (dd, J=10.2 and 14.1 Hz, 1H, —CO—CH$_2$), 2.31 (dd, J=5.4 and 14.1 Hz, 1H, —CO—CH$_2$—), 1.43 (br, 2H, piperidinyl), 1.26 (br, 4H, piperidinyl); $^{13}$C NMR (75 MHz, CDCl$_3$) δ 169.7, 153.3, 145.7, 145.2, 141.0, 129.5, 129.2, 128.2, 128.1, 126.7, 124.8, 124.6, 123.2, 123.1, 121.5, 115.0, 61.2, 47.6, 43.2, 41.7, 24.8, 24.2; HRMS (FAB, M+H) Calcd for C$_{28}$H$_{32}$N$_5$O 454.2607, found 454.2654.

EXAMPLE 8

Preparation of 4-{N-[4-(4-fluorobenzenesulfonylamido)benzyl]acetamido}-3-phenyl-2-(piperidine-1-yl)-3,4-dihydroquinazoline (10: KYS05042)

The compound (9) (0.11 g, 0.26 mmol) was dissolved in 10 ml of dichloromethane and pyridine (0.06 g, 0.76 mmol) was added thereto. 4-fluorobenzenesulfonyl chloride (0.06 g, 0.31 mmol) dissolved in 5 in 5 ml of dichloromethane at 0° C. was gently dropped to the reaction mixture and stirred for 24 hours at a room temperature. After the reaction was completed, the reaction mixture was extracted with dichloromethane three times and washed with brine. An organic layer was dried with anhydrous magnesium sulfate and the solvent was removed under reduced pressure. The reaction mixture was subjected to column chromatography (CH$_2$Cl$_2$:MeOH=10:1) to purify the title compound in the form of a white crystal (10) (0.11 g, 73%).

$^1$H NMR (300 MHz, CDCl$_3$) δ 7.66-7.62 (m, 2H, aromatic), 7.28-7.23 (m, 2H, aromatic), 7.20-7.06 (m, 9H, aromatic), 7.04-6.90 (m, 4H, aromatic), 6.72 (br, 1H, —CO—N$\underline{H}$—CH$_2$—), 5.19 (dd, J=6.0 and 9.9 Hz, 1H, —CH$_2$—C$\underline{H}$—N—), 4.41 (dd, J=6.1 and 14.8 Hz, —N$\underline{H}$—CH$_2$—), 4.24 (dd, J=5.5 and 14.8 Hz, —NH—C$\underline{H}_2$—), 3.28 (br, 4H, piperidinyl), 2.74 (dd, J=9.6 Hz and 14.1 Hz, 1H, —CO—CH$_2$), 2.44 (dd, J=6.0 and 14.1 Hz, 1H, —CO—CH$_2$—), 1.39 (br, 2H, piperidinyl), 1.25(br, 4H, piperidinyl); $^{13}$C NMR (75 MHz, CDCl$_3$) δ 170.1, 166.7, 153.9, 145.3, 141.7, 135.9, 135.0, 129.9, 129.7, 129.3, 128.9, 128.4, 126.7, 125.2, 124.8, 123.2, 121.5, 116.3, 116.0, 61.4, 47.9, 43.3, 42.0, 25.2, 24.6; HRMS (FAB, M+H) Calcd for C$_{34}$H$_{35}$FN$_5$O$_3$S 612.2445, found 612.2436.

The physicochemical properties of the compounds prepared in Examples 3 to 8 are shown in Table 1, which is provided below.

TABLE 1

| No. | Structure of compound | Physicochemical properties |
|---|---|---|
| 1 | 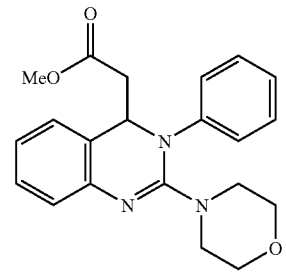 | $^1$H NMR (300 MHz, CDCl$_3$) δ 7.24-7.18(m, 4H, aromatic), 7.08-7.00(m, 3H, aromatic), 6.92-6.89(m, 2H, aromatic), 5.08(dd, J=4.8 and 10.4 Hz, 1H, —CH$_2$—C$\underline{H}$—N—), 3.69(s, 3H, —OCH$_3$), 3.55-3.43(m, 8H, morpholinyl), 2.80(dd, J=10.4 and 15.0 Hz, 1H, —CO—CH$_2$—), 2.50(dd, J=4.8 and 15.0 Hz, 1H, —CO—CH$_2$—); $^{13}$C NMR (75 MHz, CDCl$_3$) δ 172.0, 153.0, 145.8, 143.7, 129.6, 128.7, 126.1, 125.0, 124.5, 123.2. 123.1, 122.5, 66.6, 61.2. 52.1, 46.4, 40.0. |
| 2 | 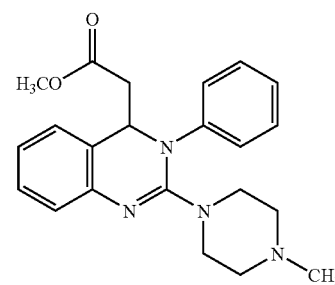 | $^1$H NMR (300 MHz, CDCl$_3$) δ 7.15-7.10(m, 4H, aromatic), 6.98(d, J=7.8 Hz, 2H, aromatic), 6.91(t, J=7.2 Hz. 1H, aromatic), 6.85-6.80(m, 2H, aromatic), 5.01(dd, J=4.5 and 10.2 Hz, 1H, —CH$_2$—C$\underline{H}$—N—), 3.62(s, 3H, —OCH$_3$), 3.38 (s, 4H, piperazinyl), 2.73(dd, J=10.2 and 15.0 Hz, 1H, —CO—CH$_2$—), 2.42(dd, J=4.5 and 15.0 Hz, 1H, —CO—CH$_2$—), 2.18-2.12(m, 7H, 1-methyl-piperazinyl); $^{13}$C NMR (75 MHz, CDCl$_3$) δ 172.0, 152.9, 145.9, 143.9, 129.5, 128.6, 126.0, 124.9, 124.3, 123.1, 122.9, 122.5, 61.2, 54.7, 52.0, 46.3, 45.8, 39.9. |
| 3 | 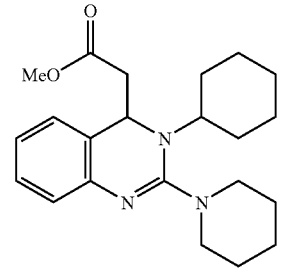 | mp 131° C.; $^1$H NMR (300 MHz, CDCl$_3$) δ 7.14(m, 1H, aromatic), 7.03(m, 1H, aromatic), 6.98(m, 1H, aromatic), 6.90(m, 1H, aromatic), 4.67(dd, J=5.1 and 9.6 Hz, 1H, —CH$_2$—C$\underline{H}$—N—), 3.62(s, 3H, —OCH$_3$), 3.42-3.36(m, 2H, piperidinyl), 3.19(m, 1H, piperidinyl), 3.10(br, 1H, —N—CH—), 2.48(dd, J=9.6 and 14.4 Hz, 1H, —CO—CH$_2$—), 2.31(dd, J=5.4 and 14.4 Hz, 1H, —CO—CH$_2$), 1.87-1.47(m, 12H, piperidinyl and cyclohexyl), 1.25-1.01(m, 5H, piperidinyl and cyclohexyl); $^{13}$C NMR (75 MHz, CDCl$_3$) δ 171.9. 157.9, 144.9, 128.2, 128.0, 124.1, 123.0, 122.6, 61.4, 51.7, 51.5, 47.7, 32.7, 31.4, 26.8, 26.5, 25.6, 25.3. |
| 4 | 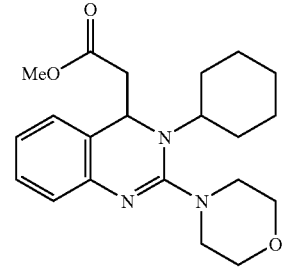 | $^1$H NMR (300 MHz, CDCl$_3$) δ 7.19(m, 1H, aromatic), 7.08(m, 1H, aromatic), 7.04(m, 1H, aromatic), 6.98(m, 1H, aromatic), 4.72(dd, J=5.4 and 9.8 Hz, 1H, —CH$_2$CH—N—), 3.72(m, 4H, morpholinyl), 3.65(s, 3H, —OCH$_3$), 3.50(m, 4H, morpholinyl), 3.24(m, 1H, —N—CH—), 2.51(dd, J=9.9 and 13.8 Hz, 1H, —CO—CH$_2$—), 2.35(dd, J=5.1 and 13.8 Hz, 1H, —CO—CH$_2$—), 1.88(m, 1H, piperidinyl), 1.74(m, 1H, piperidinyl), 1.63-1.55(m, 3H, piperidinyl), 1.29-1.05(m, 5H, piperidinyl); $^{13}$C NMR (75 MHz, CDCl$_3$) δ 172.2, 157.4, 144.1, 128.3, 127.8, 124.2, 123.3, 123.1, 67.1, 61.4, 51.8, 51.5, 40.8, 32.7, 31.4, 26.7, 26.4, 25.5. |
| 5 | 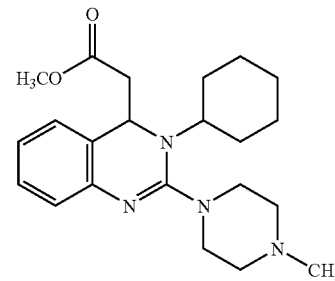 | $^1$H NMR (300 MHz, CDCl$_3$) δ 7.18(m, 1H, aromatic), 7.07(m, 1H, aromatic), 7.02(m, 1H, aromatic), 6.96(m, 1H, aromatic), 4.71(dd, J=5.1 and 9.5 Hz, 1H, —CH$_2$—C$\underline{H}$—N—), 3.65(s, 3H, —OCH$_3$), 3.58(br, 1H, —N—CH—), 3.43(br, 2H, piperazinyl), 3.27-3.23(m, 2H, piperaziny), 2.63(br, 2H, piperaziny), 2.50(dd, J=9.6 and 14.0 Hz, 1H, —CO—CH$_2$—), 2.37-2.26(m, 6H, —CO—CH$_2$—, piperazinyl, and —N—CH$_3$), 1.89-1.76(m, 2H, cyclohexyl), 1.60-1.54(m, 3H, cyclohexyl), 1.29-1.04(m, 5H, cyclohexyl); $^{13}$C NMR (75 MHz, CDCl$_3$) δ 171.7, 157.4, 144.5, 128.2, 127.9, 124.1. 123.1, 123.0, 61.4, 55.3, 51.7, 51.5, 46.5, 40.7, 32.7, 31.4, 26.7, 26.4, 25.6. |

TABLE 1-continued

| No. | Structure of compound | Physicochemical properties |
|---|---|---|
| 6 | (structure) | mp 96° C.; $^1$H NMR (300 MHz, CDCl$_3$) δ 7.16(m, 1H, aromatic), 7.07(m, 1H, aromatic), 7.01(m, 1H, aromatic), 6.93(m, 1H, aromatic), 4.69(dd, J=5.4 and 9.5 Hz, 1H, —CH$_2$—C$\underline{H}$—N—), 3.71(sept, J=7.2 Hz, 1H, —N—C$\underline{H}$—(CH$_3$)$_2$), 3.65(s, 3H, —OCH$_3$), 3.44-3.84(m, 3H, piperidinyl), 3.13(br, 1H, piperidinyl), 2.51(dd, J=9.6 and 13.8 Hz, 1H, —CO—CH$_2$—), 2.35(dd, J=5.4 and 14.1 Hz, 1H, —CO—CH$_2$—), 1.54(br, 6H, piperidinyl), 1.22(d, J=7.2 Hz, 3H, —N—CH—(C$\underline{H}_3$)$_2$), 0.78(d, J=6.9 Hz, 3H, —N—CH—(C$\underline{H}_3$)$_2$); $^{13}$C NMR (75 MHz, CDCl$_3$) δ 171.7, 157.8, 144.7, 128.1, 127.9, 124.0, 123.0, 122.7, 52.4, 51.6, 50.3, 40.6, 26.1, 25.2, 21.9, 20.7. |
| 7 | (structure) | $^1$H NMR (300 MHz, CDCl$_3$) δ 7.11(m, 1H, aromatic), 7.01(m, 1H, aromatic), 6.97(m, 1H, aromatic), 6.90(m, 1H, aromatic), 4.65(dd, J=5.1 and 9.6 Hz, 1H, —CH$_2$C$\underline{H}$—N—), 3.73-3.64(m, 5H, —N—C$\underline{H}$—(CH$_3$)$_2$ and morpholinyl), 3.58(s, 3H, —OCH$_3$), 3.44(br, 4H, morpholinyl), 2.44(dd, J=9.9 and 13.8 Hz, 1H, —CO—CH$_2$—), 2.30(dd, J=5.1 and 14.1 Hz, 1H, —CO—CH$_2$—), 1.15(d, J=6.6 Hz, 3H, —N—CH—(C$\underline{H}_3$)$_2$), 0.73(d, J=6.0 Hz, 3H, —N—CH—(C$\underline{H}_3$)$_2$); $^{13}$C NMR (75 MHz, CDCl$_3$) δ 171.4, 157.3, 144.1, 128.3, 127.8, 124.1, 123.3, 123.1, 67.0, 52.4, 51.7, 50.3, 40.7, 21.9, 20.7, |
| 8 | (structure) | $^1$H NMR (300 MHz, CDCl$_3$) δ 7.09(m, 1H, aromatic), 7.01(m, 1H, aromatic), 6.94(m, 1H, aromatic), 6.87(m, 1H, aromatic), 4.62(dd, J=5.1 and 9.6 Hz, 1H, —CH$_2$C$\underline{H}$—N—), 3.65(sept, J=6.6 Hz, 1H, —N—C$\underline{H}$—(CH$_3$)$_2$), 3.56(s, 3H, —OCH$_3$), 3.40(br, 4H, piperazinyl), 2.46(br, 4H, piperazinyl), 2.42(dd, J=9.3 and 14.4 Hz, 1H, —CO—CH$_2$—), 2.31-2.25(m, 4H, —CO—CH$_2$— and —N—CH$_3$), 1.14(d, J=6.6 Hz, 3H, —N—CH—(C$\underline{H}_3$)$_2$), 0.71(d, J=6.6 Hz, 3H, —N—CH—(C$\underline{H}_3$)$_2$); $^{13}$C NMR (75 MHz, CDCl$_3$) δ 171.5, 157.2, 144.0, 128.3, 127.8. 124.1, 123.1, 123.0, 55.2, 52.5, 51.7, 5.03, 46.4, 40.7, 21.9, 20.7. |
| 9 | (structure) | $^1$H NMR (300 MHz, CDCl$_3$) δ 7.26-7.18(m, 4H, aromatic), 7.04–6.99(m, 3H, aromatic), 6.94–6.88(m, 2H, aromatic), 5.10(dd, J=4.6 and 10.7 Hz, 1H, —CH$_2$—C$\underline{H}$—N—), 3.75(s, 3H, —OCH$_3$), 2.88(s, 6H, —N—Me$_2$), 2.83(dd, J=10.7 and 15.1 Hz, 1H, —CO—CH$_2$—), 2.50(dd, J=4.5 and 15.0 Hz, 1H —CO—CH$_2$—); $^{13}$C NMR (75 MHz, CDCl$_3$) δ 171.9, 153.5, 145.8, 144.0, 129.3, 128.3, 125.3, 124.7, 123.8, 122.8, 122.0, 121.8, 61.2, 51.8, 39.7, 37.6. |
| 10 | (structure) | $^1$H NMR (300 MHz, CDCl$_3$) δ 7.16(m, 1H, aromatic), 7.21-7.09(m, 2H, aromatic), 7.02-6.91(m, 2H, aromatic), 4.62(dd, J=4.5 and 10.2 Hz, 1H, —CH$_2$—C$\underline{H}$—N—), 3.67(s, 3H, —OCH$_3$), 3.36-3.27(m, 5H, piperidinyl and —N—C$\underline{H}_2$—CH$_3$), 3.08(m, 1H, —N—C$\underline{H}_2$—CH$_3$), 2.61(dd, J=9.9 and 14.7 Hz, 1H, —CO—CH$_2$—), 2.34(dd, J=4.6 and 15.1 Hz, 1H, —CO—CH$_2$—), 1.63(br, 6H, piperidinyl), 1.00(t, J=7.2 Hz, 3H, —N—CH$_2$—C$\underline{H}_3$); $^{13}$C NMR (75 MHz, CDCl$_3$) δ 171.7, 157.2, 144.4, 128.0, 126.3, 124.1, 122.7, 122.4, 55.3, 51.4, 47.2, 39.9, 25.8, 24.8, 14.0. |

TABLE 1-continued

| No. | Structure of compound | Physicochemical properties |
|---|---|---|
| 11 | 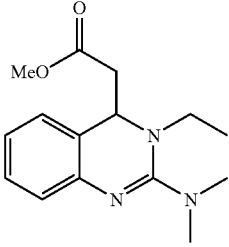 | $^1$H NMR (300 MHz, CDCl$_3$) δ 7.21-7.11(m, 2H, aromatic), 7.02-6.91(m, 2H, aromatic), 4.61(dd, J=4.8 and 10.5 Hz, 1H, —CH$_2$—C<u>H</u>—N—), 3.67(s, 3H, —OCH$_3$), 3.21(m, 1H, 3.13 —N—C<u>H</u>$_2$—CH$_3$), 3.03(m, 1H, —N—C<u>H</u>$_2$—CH$_3$), 2.96(s, 6H, —NMe$_2$), 2.59(dd, J=9.9 and 14.7 Hz, 1H, —CO—CH$_2$—), 2.34(dd, J=4.7 and 15.1 Hz, 1H, —CO—CH$_2$—), 1.00(t, J=7.2 Hz, 3H, —N—CH$_2$—C<u>H</u>$_3$); $^{13}$C NMR (75 MHz, CDCl$_3$) δ 171.5, 157.4, 144.1, 128.0, 125.7, 124.2, 122.5, 122.2, 55.5, 51.3, 46.9, 39.9, 38.4, 13.8. |
| 12 | 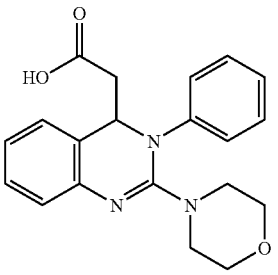 | mp 237° C.; $^1$H NMR (300 MHz, DMSO) δ 7.59(d, J=7.8 Hz, 1H aromatic), 7.48-7.39(m, 5H, aromatic), 7.31-7.31(m, 2H, aromatic), 7.21(m, 1H, aromatic), 5.32(dd, J=6.3 and 8.2 Hz, 1H, —CH$_2$—C<u>H</u>—N—), 3.60-3.48(m, 4H, morpholinyl), 3.40-3.33(m, 4H, morpholinyl), 2.98(dd, J=8.2 and 15.6 Hz, 1H, —CO—CH$_2$—), 2.72(dd, J=6.3 and 15.1 Hz, 1H, —CO—CH$_2$—); $^{13}$C NMR (75 MHz, DMSO) δ 175.8, 157.1, 147.0, 136.1, 134.4, 133.5, 131.9, 130.7, 130.2, 129.9, 128.4, 122.0, 69.3, 65.6, 52.7, 50.9, 44.0. |
| 13 | 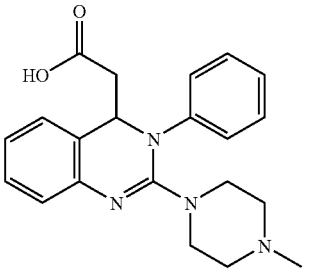 | $^1$H NMR (300 MHz, CD$_3$OD) δ 7.31-7.15(m, 7H, aromatic), 7.10-7.08(m, 2H, aromatic), 5.11(dd, J=5.4 and 9.8 Hz, 1H, —CH$_2$—C<u>H</u>—N—), 3.39-3.32(m, 4H, piperazinyl), 2.57-2.31(m, 6H, —CO—CH$_2$—, and piperazinyl), 2.24(s, 3H, —N—CH$_3$); $^{13}$C NMR (75 MHz, CD$_3$OD) δ 175.6, 153.2, 144.0, 135.4, 129.9, 128.8, 127.6, 126.8, 125.6, 125.4, 124.2, 119.1, 63.0, 53.2, 46.7, 44.2, 43.2. |
| 14 | 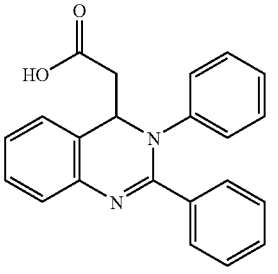 | mp 245° C.; $^1$H NMR (300 MHz, DMSO) δ 7.73-7.71(m, 2H, aromatic), 7.39-7.28 (m, 5H, aromatic), 7.22-7.13(m, 4H, aromatic), 7.03-6.94(m, 3H, aromatic), 5.35 (dd, J=6.7 and 8.4 Hz, 1H, —CH$_2$—C<u>H</u>—N—), 2.75(dd, J=8.3 and 14.9 Hz, 1H, —CO—CH$_2$—), 2.54(dd, J=6.2 and 14.9 Hz, 1H, —CO—CH$_2$—); $^{13}$C NMR (75 MHz, DMSO) δ 172.3, 154.7, 145.7, 142.1, 136.3, 130.9, 130.1, 129.7, 129.0, 128.9, 127.4, 126.7, 126.1, 124.8, 124.6, 123.8, 59.3, 41.2. |
| 15 | 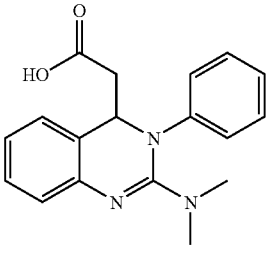 | $^1$H NMR (300 MHz, CDCl$_3$) δ 7.73(d, J=8.1 Hz, 1H, aromatic), 7.38-7.33(m, 2H, aromatic), 7.27-7.21(m, 4H, aromatic), 7.12(d, J=3.9 Hz, 2H, aromatic), 5.23(dd, J=4.8 and 9.3 Hz, 1H, —CH$_2$—C<u>H</u>—N—), 2.97(s, 6H, —N—Me$_2$), 2.83(dd, J=9.3 and 14.4 Hz, 1H, —CO—CH$_2$—), 2.60(dd, J=4.9 and 14.3 Hz, 1H, —CO—CH$_2$). |

TABLE 1-continued

| No. | Structure of compound | Physicochemical properties |
|---|---|---|
| 16 | 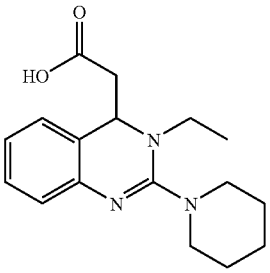 | $^1$H NMR (300 MHz, CDCl$_3$) δ 7.28(d, J=7.8 Hz, 1H, aromatic), 7.20-7.15(m, 2H, aromatic), 7.08(m, 1H, aromatic), 4.94(dd, J=6.0 and 8.7 Hz, 1H, —CH$_2$—C$\underline{H}$—N—), 3.51(m, 1H, —N—C$\underline{H}_2$—CH$_3$), 3.38-3.25(m, 5H, piperidinyl and —N—C$\underline{H}_2$—CH$_3$), 2.42(dd, J=8.8 and 14.8 Hz, 1H, —CO—CH$_2$—), 2.22(dd, J=5.6 and 14.8 Hz, 1H, —CO—CH$_2$—), 1.49(br, 6H, piperidinyl), 1.09(t, J=7.2 Hz, 3H, —N—CH$_2$—C$\underline{H}_3$). |
| 17 | 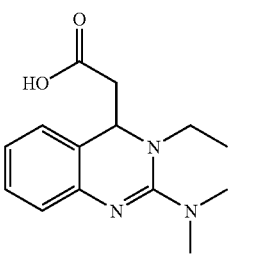 | $^1$H NMR (300 MHz, CDCl$_3$ and CD$_3$OD) δ 7.42(d, J=7.8 Hz, 1H, aromatic), 7.30-7.26(m, 2H, aromatic), 7.18(m, 1H, aromatic), 5.00(dd, 15.1 and 9.6 Hz, 1H, —CH$_2$—C$\underline{H}$—N—), 3.65-3.41(m, 2H, —N—C$\underline{H}_2$—CH$_3$), 3.17(s, 6H, —NMe$_2$), 2.54(dd, J=9.6 and 15.0 Hz, 1H, —CO—CH$_2$—), 2.41(dd, J=5.4 and 14.7 Hz, 1H, —CO—CH$_2$—), 1.16(t, J=7.2 Hz, 3H, —N—CH$_2$C$\underline{H}_3$). |
| 18 | 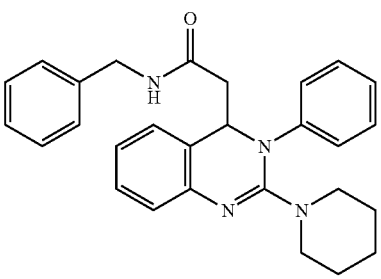 | mp 168° C.; $^1$H NMR (300 MHz, CDCl$_3$) δ 7.71(br, 1H, —CO—N$\underline{H}$—CH$_2$—Ph), 7.35-7.31(m, 2H, aromatic), 7.29-7.19(m, 5H, aromatic), 7.16-7.03(m, 5H, aromatic), 6.96-6.92(m, 2H, aromatic), 5.18(dd, J=5.0 and 10.1 Hz, 1H, —CH$_2$—C$\underline{H}$—N—), 4.53(dd, J=6.0 and 14.4 Hz, 1H, —NH—C$\underline{H}_2$—Ph), 4.42(dd, J=6.3 and 14.4 Hz, 1H, —NH—C$\underline{H}_2$—Ph), 3.17(br, 4H, piperidinyl), 2.68(dd, J=10.1 and 14.0 Hz, 1H, —CO—CH$_2$—), 2.23(dd, J=5.0 and 14.1 Hz, 1H, —CO—CH$_2$—), 1.37-1.33(m, 2H, piperidinyl), 1.18(br, 4H, piperidinyl); $^{13}$C NMR (75 MHz, CDCl$_3$) δ 170.4. 153.9, 146.1, 143.2, 138.6, 129.3, 128.8, 128.5, 128.4, 127.7, 127.0, 125.2, 124.9, 124.4, 123.2, 122.8, 122.3, 61.1, 47.4, 43.9, 41.9, 25.3, 24.7; HRMS(FAB, M + H)Calcd for C$_{28}$H$_{31}$N$_4$O 439.2498, found 439.2534. |
| 19 | 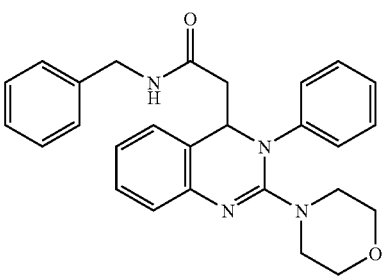 | mp 138° C.; $^1$H NMR (300 MHz, CDCl$_3$ and CD$_3$OD) δ 7.91(br, 1H, —N$\underline{H}$—Bn), 7.31-7.19(m, 8H, aromatic), 7.12-7.05(m, 4H, aromatic), 7.01-6.93(m, 2H, aromatic), 5.18(dd, J=4.8 and 10.8 Hz, 1H, —CH$_2$—C$\underline{H}$—N—), 4.48(dd, J=5.5 and 14.2 Hz, 1H, —NH—C$\underline{H}_2$—Ph), 4.32(dd, J=5.5 and 14.2 Hz, 1H, —NH—C$\underline{H}_2$—Ph), 3.37-3.21(m, 8H, morpholinyl), 2.53(dd, J=10.5 and 14.1 Hz, 1H, —CO—CH$_2$—), 2.36(dd, J=4.6 and 13.9 Hz, 1H, —CO—CH$_2$—); $^{13}$C NMR (75 MHz, CDCl$_3$) δ 170.6, 154.1, 145.3, 142.9, 138.4, 129.5, 128.8, 128.5, 127.7, 127.2, 125.1, 124.9, 123.5, 123.1, 122.5, 66.2, 61.4, 46.5, 44.0, 41.7; HRMS (FAB, M + H) Calcd for C$_{27}$H$_{29}$N$_4$O$_2$ 441.2291, found 441.2290. |
| 20 | 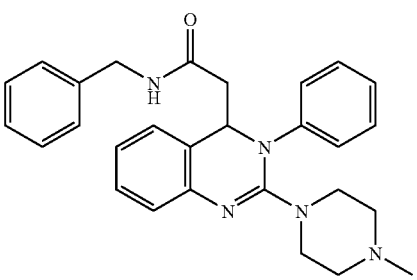 | mp 186° C.; $^1$H NMR (300 MHz, CDCl$_3$) δ 7.28-7.19(m, 7H, aromatic), 7.17-7.11 (m, 3H, aromatic), 7.09-7.01(m, 2H, aromatic), 6.96-6.87(m, 2H, aromatic), 6.68 (t, J=5.4 Hz, 1H, —CO—N$\underline{H}$—CH$_2$—Ph), 5.20(dd, J=5.4 and 9.3 Hz, 1H —CH$_2$—C$\underline{H}$—N—), 4.50(dd, J=5.8 and 14.5 Hz, 1H, —NH—C$\underline{H}_2$—Ph), 4.42(dd, J=5.8 and 14.5 Hz, 1H, —NH—C$\underline{H}_2$—Ph), 3.27(br, 4H, piperazinyl), 2.55(dd, J=9.6 and 14.1 Hz, 1H, —CO—CH$_2$—), 2.34(dd, J=5.7 and 14.4 Hz, 1H, —CO—CH$_2$—), 2.14(s, 3H, —N—CH$_3$), 2.11-2.04(m, 4H, piperazinyl); $^{13}$C NMR (75 MHz, CDCl$_3$) δ 170.2, 153.5, 145.8, 143.4, 138.3, 129.4, 128.9, 128.5, 128.4, 127.8, 126.7, 125.2, 124.6, 123.1, 123.0, 122.7, 61.2, 54.4, 46.3, 46.1, 44.0, 42.1; HRMS (FAB, M + H) Calcd for C$_{28}$H$_{32}$N$_5$O 454.2607, found 454.2600. |

TABLE 1-continued

| No. | Structure of compound | Physicochemical properties |
|---|---|---|
| 21 | | mp 204° C.; $^1$H NMR (300 MHz, DMSO) δ 8.61(t, J=5.1 Hz, 1H, —N<u>H</u>—CH$_2$—Ph), 7.68(d, J=7.2 Hz, 2H, aromatic), 7.40-7.20(m, 9H, aromatic), 7.17-7.10(m, 4H, aromatic), 7.04-6.92(m, 3H, aromatic), 5.39(dd, J=5.4 and 8.4 Hz, 1H, —CH$_2$—C<u>H</u>—N—), 4.41(dd, J=5.4 and 14.7 Hz, 1H, —NH—C<u>H</u>$_2$—Ph), 4.30(dd, J=5.1 and 15.0 Hz, —NH—C<u>H</u>$_2$—Ph), 2.77(dd, J=9.0 and 13.8 Hz, 1H, —CO—CH$_2$—), 2.43(dd, J=5.3 and 14.2 Hz, 1H, —CO—CH$_2$—); $^{13}$C NMR (75 MHz, DMSO) δ 169.7, 154.8, 145.9, 142.3, 139.8, 136.7, 130.7, 130.3, 129.5, 129.0, 128.8, 128.4, 127.9, 127.6, 126.6, 126.0, 124.8, 124.4, 123.9, 59.9, 43.1, 42.3, |
| 22 | | $^1$H NMR (300 MHz, CDCl$_3$) δ 7.36-7.30(m, 5H, aromatic). 7.20-7.15(m, 4H, aromatic), 7.02-6.97(m, 3H, aromatic), 6.91-6.87(m, 2H, aromatic), 5.18(s, 2H, —O—C<u>H</u>$_2$—Ph), 5.07(dd, J=4.8 and 10.2 Hz, 1H, —CH$_2$—C<u>H</u>—N—), 3.31(br, 4H, piperidinyl), 2.84(dd, J=10.5 and 15.3 Hz, 1H, —CO—CH$_2$—), 2.52(dd, J=4.7 and 14.9 Hz, 1H, —CO—CH$_2$—), 1.45-1.40(m, 2H, piperidinyl), 1.30-1.21(m, 4H, piperidinyl); $^{13}$C NMR (75 MHz, CDCl$_3$) δ 171.5, 153.5, 146.2, 144.2, 135.8, 129.4, 128.9, 128.7, 128.6, 127.2, 126.1, 125.0, 124.2, 123.0, 122.8, 122.5, 66.9, 61.2, 47.1, 40.0, 25.6, 25.0. |
| 23 | | $^1$H NMR (300 MHz, CDCl$_3$) δ 7.37-7.31(m, 5H, aromatic), 7.23-7.17(m, 4H, aromatic), 7.04-6.99(m, 3H, aromatic), 6.92-6.90(m, 2H, aromatic), 5.23(d, J=12.3 Hz, —O—C<u>H</u>$_2$—Ph), 5.12(d, J=12.3 Hz, —O—C<u>H</u>$_2$—Ph), 5.07(dd, J=4.4 and 10.7 Hz, 1H, —CH$_2$—C<u>H</u>—N—), 3.42-3.30(m, 8H, morpholinyl), 2.81d(dd, J=10.5 and 15.0 Hz, 1H, —CO—CH$_2$—), 2.51(dd, J=4.4 and 15.1 Hz, 1H, —CO—CH$_2$—): $^{13}$C NMR (75 MHz, CDCl$_3$) δ 171.4, 153.2, 145.7, 143.6, 135.7, 129.5, 129.1, 128.9, 128.7, 127.7, 127.2, 126.1, 125.0, 124.6, 123.2, 122.6, 66.5, 65.2, 61.3, 46.4, 40.2. |
| 24 | | $^1$H NMR (300 MHz, CDCl$_3$) δ 7.36-7.31(m, 5H, aromatic), 7.22-7.15(m, 4H, aromatic), 7.03-7.00(m, 3H, aromatic), 6.93-6.89(m, 2H, aromatic), 5.21(d, J=12.0 Hz, 1H, —O—C<u>H</u>$_2$—Ph), 5.15(d, J=12.3 Hz, 1H, —O—C<u>H</u>$_2$—Ph), 5.08(dd, J=4.8 and 10.2 Hz, 1H, —CH$_2$—C<u>H</u>—N—), 3.27(br, 4H, piperazinyl), 2.86(dd, J=10.5 and 15.0 Hz, 1H, —CO—CH$_2$—), 2.54(dd, J=4.7 and 15.4 Hz, 1H, —CO—CH$_2$—), 2.17(s, 3H, —N—CH$_3$), 2.14(br, 4H, piperazinyl); $^{13}$C NMR (75 MHz, CDCl$_3$) δ 171.4, 153.0, 145.9, 143.9, 135.7, 129.4, 129.0, 128.9, 128.8, 128.7, 126.0, 125.0, 124.4, 123.2, 122.8, 122.6, 67.0, 61.2, 54.7, 46.3, 45.8, 40.1. |
| 25 | | $^1$H NMR (300 MHz, CDCl$_3$) δ 7.71-7.68(m, 2H, aromatic), 7.50(d, J=7.2 Hz, 1H, aromatic), 7.34-7.15(m, 9H, aromatic), 7.13-7.03(m, 4H, aromatic), 7.01-6.92(m, 3H, aromatic), 5.39(dd, J=6.3 and 7.8 Hz, 1H, —CH$_2$—C<u>H</u>—N—), 5.22(d, J=12.3 Hz, 1H, —O—C<u>H</u>$_2$—Ph), 5.13(d, J=12.0 Hz, 1H, —O—C<u>H</u>$_2$—Ph), 2.95(dd, J=8.1 and 15.0 Hz, 1H, —CO—CH$_2$—), 2.72(dd, J=6.4 and 14.6 Hz, 1H, —CO—CH$_2$—); $^{13}$C NMR (75 MHz, CDCl$_3$) δ 171.0, 155.0, 145.4, 142.1, 136.3, 135.7, 130.4, 130.0, 129.2, 128.9, 128.8, 128.7, 128.5, 126.4, 125.3, 125.1, 124.4, 123.7, 67.1, 59.5, 41.0. |

TABLE 1-continued

| No. | Structure of compound | Physicochemical properties |
|---|---|---|
| 26 | 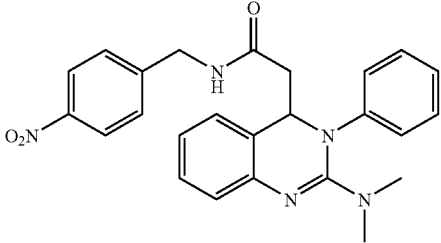 | $^1$H NMR (300 MHz, CDCl$_3$ and CD$_3$OD) δ 8.14-8.10(m, 2H, aromatic), 7.39(d, J= 8.7 Hz, 2H, aromatic), 7.30-7.13(m, 4H, aromatic), 7.08-7.03(m, 3H, aromatic), 6.98-6.89(m, 2H, aromatic), 5.20(dd, J=6.0 and 9.3 Hz, 1H, —CH$_2$—CH—N—), 4.59(d, J=15.6 Hz, 1H, —NH—CH$_2$—), 4.36(d, J=15.3 Hz, 1H,—NH—CH$_2$—), 2.78(s, 6H, —NMe$_2$), 2.63(dd, J =9.6 and 13.8 Hz, 1H, —CO—CH$_2$—), 2.43(dd, J=6.0 and 13.8 Hz, 1H, —CO—CH$_2$—); $^{13}$C NMR (75 MHz, CDCl$_3$ and CD$_3$OD) δ 170.6, 154.4, 147.0, 145.8, 145.0, 142.7, 129.4, 128.4, 128.3, 126.3, 125.0, 124.4, 123.6, 122.7, 122.2, 121.9, 61.1, 42.7, 41.2, 37.8. |
| 27 | 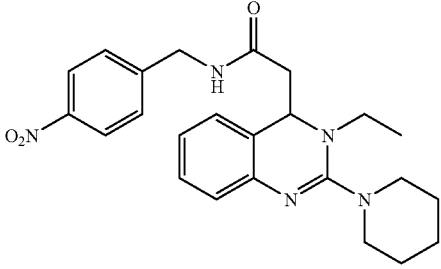 | $^1$H NMR (300 MHz, CDCl$_3$)δ 9.19(t, J=5.4 Hz, 1H, —CO—NH—CH$_2$—), 8.11(d, J=8.7 Hz, 2H, —CH$_2$—C$_4$H$_4$—NO$_2$), 7.57(d, J=9.0 Hz, 2H, —CH$_2$—C$_4$H$_4$—NO$_2$), 7.18-7.07(m, 4H, aromatic), 4.89(dd, J=4.1 and 10.7 Hz, 1H, —CH$_2$—CH—N—), 4.49(dd, J=4.7 and 13.4 Hz, 1H, —NH—CH$_2$—), 4.43(dd, J=4.7 Hz and 13.4 Hz, 1H, —NH—CH$_2$—), 3.48-3.20(m, 6H, piperidinyl and —N—CH$_2$CH$_3$), 2.89(dd, J=10.9 and 14.8 Hz, 1H, —CO—CH$_2$), 2.08(dd, J=4.1 and 14.6 Hz, 1H, —CO—CH$_2$—), 1.52(br, 6H, piperidinyl), 1.07(t, J=7.2 Hz, 3H —N—CH$_2$CH$_3$); $^{13}$C NMR (75 MHz, CDCl$_3$) δ 177.3, 170.1, 156.7, 146.3, 138.4, 128.6, 128.5, 127.2, 124.4, 124.3, 123.5, 120.2, 55.1, 47.5, 42.6, 41.2, 25.3, 24.1, 23.3, 14.2. |
| 28 | 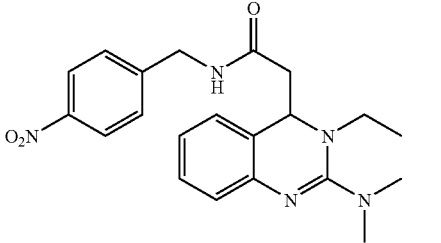 | $^1$H NMR (300 MHz, CDCl$_3$) δ 9.26(t, J=6.0 Hz, 1H, —CO—NH—CH$_2$—), 8.12(d, J=8.7 Hz, 2H, aromatic), 7.62-7.55(m, 3H, aromatic), 7.17-7.09(m, 3H, aromatic), 4.85(dd, J=4.2 and 10.8 Hz, 1H, —CH$_2$—CH—N—), 4.49-4.46(m, 2H, —NH—CH$_2$—), 3.28-3.22(m, 2H, —N—CH$_2$CH$_3$), 3.05(s, 6H, —NMe$_2$), 2.83(dd, J=10.9 and 14.3 Hz, 1H,) —CO—CH$_2$, 2.05(dd, J=3.9 and 14.4 Hz, 1H, —CO—CH$_2$—), 1.06(t, J=7.2 Hz, 3H, —N—CH$_2$CH$_3$); $^{13}$C NMR (75 MHz, CDCl$_3$) δ 169.6, 155.9 147.0 146.3, 134.3, 129.1, 128.6, 126.4, 125.7, 124.4, 123.4, 119.1, 55.9, 48.1, 42.6, 41.3, 40.6, 14.0. |
| 29 | 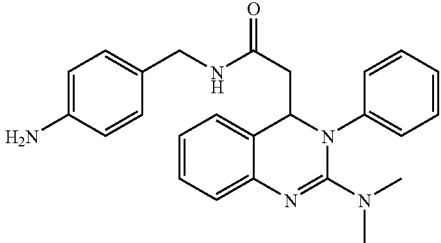 | $^1$H NMR (300 MHz, CDCl$_3$) δ 7.35(t, J=5.6 Hz, 1H, —CO—NH—CH$_2$), 7.26-7.20 (m, 2H, aromatic), 7.14-6.99(m, 6H, aromatic), 6.92-6.83(m, 2H, aromatic), 6.57-6.54(m, 2H, aromatic), 5.20(dd, J=5.1 and 9.9 Hz, 1H, —CH$_2$—CH—N—), 4.41(dd, J=5.6 and 14.3 Hz, 1H, —NH—CH$_2$—), 4.32(dd, J=5.6 and 14.3 Hz, 1H, —NH—CH$_2$—), 3.67(br, 2H, —C$_4$H$_4$—NH$_2$), 2.66(s, 6H, —NMe$_2$), 2.50(dd, J=9.9 and 14.4 Hz, 1H, —CO—CH$_2$), 2.25(dd, J=5.1 and 14.1 Hz, 1H, —CO—CH$_2$—); $^{13}$C NMR (75 MHz, CDCl$_3$) δ 170.0, 153.9, 145.7, 145.6, 143.1, 129.4, 129.2, 128.0, 126.2, 124.9, 123.9, 122.3, 122.2, 121.9, 115.0, 61.2, 43.3, 41.6, 37.9. |
| 30 | 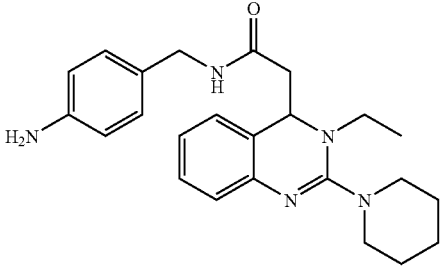 | $^1$H NMR (300 MHz, CDCl$_3$) δ 8.24(br, 1H O═C—NH—CH$_2$—), 7.08-7.03(m, 3H, aromatic), 6.97-6.84(m, 3H, aromatic), 6.57(d, J=8.1 Hz, 2H, —CH$_2$—C$_4$H$_4$—NO$_2$), 4.78(dd, J=5.6 and 8.9 Hz, 1H, —CH$_2$—CH—N—), 4.37(dd, J=6.1 and 14.3 Hz, 1H, —NH—CH$_2$—), 4.24(dd, J=5.6 Hz and 14.3 Hz, 1H, —NH—CH$_2$—), 3.27(m, 1H, —N—CH$_2$CH$_3$), 3.18-3.01(m, 5H, piperidinyl and —N—CH$_2$CH$_3$), 2.26(dd, J=9.4 and 14.3 Hz, 1H, —CO—CH$_2$), 2.01(dd, J=5.6 and 14.3 Hz, 1H, —CO—CH$_2$—), 1.43(br, 6H, piperidinyl, 0.98(t, J=6.9 Hz, 3H —N—CH$_2$CH$_3$); $^{13}$C NMR (75 MHz, CDCl$_3$) δ 169.5, 157.0, 145.3, 142.0, 129.0, 128.1, 127.4, 127.0, 123.9, 122.6, 121.1, 114.5, 76.4, 54.6, 46.8, 42.6, 41.3, 25.2, 24.1, 13.9. |

TABLE 1-continued

| No. | Structure of compound | Physicochemical properties |
|---|---|---|
| 31 | 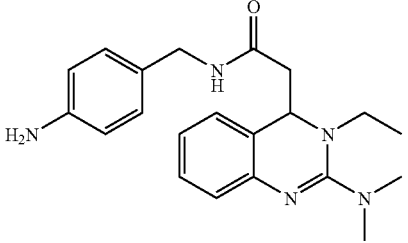 | $^1$H NMR (300 MHz, CDCl$_3$) δ 8.13(br, 1H, —CO—N<u>H</u>—CH$_2$—), 7.14-7.07(m, 4H, aromatic), 6.97(dd, J=4.1 Hz, 2H, aromatic), 6.50(d, J=8.3 Hz, 2H, aromatic), 4.78(dd, J=4.4 and 10.7 Hz, 1H, —CH$_2$—C<u>H</u>—N—), 4.36(dd, J=6.2 and 14.1 Hz, 1H, —CO—NH—C<u>H</u>$_2$—), 4.19(dd, J=5.5 and 14.1 Hz, 1H, —CO—NH—C<u>H</u>$_2$—), 3.19-3.13(m, 2H, —N—C<u>H</u>$_2$CH$_3$), 2.76 (s, 6H, —NMe$_2$), 2.41(dd, J=10.9 and 14.2 Hz, 1H, —CO—CH$_2$), 2.02(dd, J=4.4 and 14.2 Hz, 1H, —CO—CH$_2$—), 0.98(t, J=7.1 Hz, 3H, —N—CH$_2$C<u>H</u>$_3$). |
| 32 | 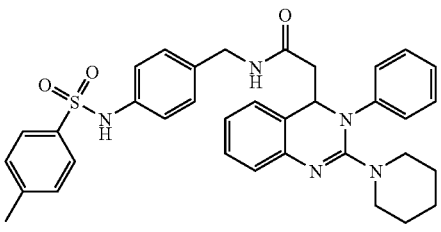 | $^1$H NMR (300 MHz, CDCl$_3$) δ 7.66(d, J=8.4 Hz, 1H, aromatic), 7.58-7.73(m, 3H, aromatic), 7.28-7.21(m, 3H, aromatic), 7.18-6.95(m, 12H, aromatic), 5.19(dd, J=5.2 and 10.1 Hz, 1H, —CH$_2$—C<u>H</u>—N—), 4.35(dd, J=6.1 and 14.2 Hz, 1H, —NH—C<u>H</u>$_2$—), 4.24(dd, J=5.5 and 14.8 Hz, 1H, —NH—C<u>H</u>$_2$—), 3.28(br, 4H, piperidinyl), 2.82(dd, J=10.5 and 14.4 Hz, 1H, —CO—CH$_2$), 2.36(dd, J=5.2 and 14.0 Hz, 1H, —CO—CH$_2$—), 2.29(s, 3H, —SO$_2$—C$_4$H$_4$—C<u>H</u>$_3$), 1.33(br, 2H, piperidinyl), 1.20(br, 4H, piperidinyl); $^{13}$C NMR (75 MHz, CDCl$_3$) δ 170.4, 154.0, 144.9, 143.6, 138.9, 136.9, 136.7, 134.7, 129.8, 129.2, 129.0, 128.9, 127.3, 126.2, 125.9, 125.4, 124.4, 124.0, 121.1, 121.0, 61.7, 48.6, 43.2, 41.9, 24.8, 24.2, 21.7; HRMS (FAB, M + H) Calcd for C$_{35}$H$_{38}$N$_5$O$_3$S 608.2695, found 608.2680. |
| 33 | 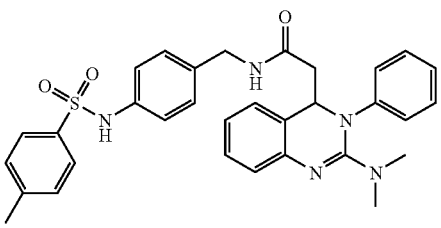 | $^1$H NMR (300 MHz, DMSO) δ 10.2(br, 1H, Ts—NH—), 8.52(t, J=5.6 Hz, 1H, —CO—N<u>H</u>—CH$_2$), 7.62(d, J=8.1 Hz, 2H, aromatic), 7.33-7.23(m, 4H, aromatic), 7.15-7.05(m, 3H, aromatic), 7.01-6.96(m, 7H, aromatic), 6.82(m, 1H, aromatic), 5.08(dd, J=4.4 and 10.4 Hz, 1H, —CH$_2$—C<u>H</u>—N—), 4.26(dd, J=6.0 and 14.7 Hz, 1H, —NH—C<u>H</u>$_2$—), 4.17(dd, J=5.6 and 14.8 Hz, 1H, —NH—C<u>H</u>$_2$—), 2.63(s, 6H, —NMe$_2$), 2.52(m, 1H, —CO—CH$_2$), 2.33(s, 3H, —SO$_2$—C$_4$H$_4$—C<u>H</u>$_3$), 2.24(dd, J=4.1 and 14.0 Hz, 1H, —CO—CH$_2$—); $^{13}$C NMR (75 MHz, DMSO) δ 169.4, 152.9, 145.8, 143.9, 143.1, 136.7, 136.4, 134.8, 129.6, 129.2, 128.5, 127.7, 126.6, 126.2, 124.8, 123.2, 122.0, 121.5, 121.1, 119.7, 60.8, 41.7, 40.8, 37.2, 20.9. |
| 34 | 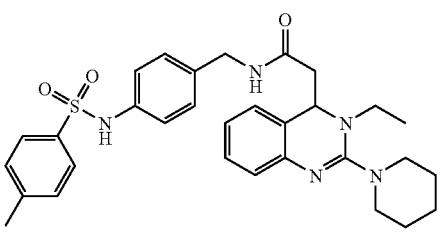 | $^1$H NMR (300 MHz, CDCl$_3$) δ 8.28(t, J=5.5 Hz, 1H, —CO—N<u>H</u>—CH$_2$—), 7.72(d, J=8.4 Hz, 2H, aromatic), 7.63(d, J=7.8 Hz, 1H, aromatic), 7.18-7.02(m, 9H, aromatic), 4.99(dd, J=5.0 and 10.4 Hz, 1H, —CH$_2$C<u>H</u>—N—), 4.22(m, 2H, —NH—C<u>H</u>$_2$—), 3.38-3.22(m, 6H, piperidinyl and —N—C<u>H</u>$_2$CH$_3$), 2.83(dd, J=10.5 and 14.1 Hz, 1H, —CO—CH$_2$), 2.29(s, 3H, —SO$_2$—C$_4$H$_4$—C<u>H</u>$_3$), 2.22(dd, J=4.7 and 14.2 Hz, 1H, —CO—CH$_2$—), 1.45(br, 6H, piperidinyl), 1.09(t, J=7.0 Hz, 3H —N—CH$_2$C<u>H</u>$_3$); $^{13}$C NMR (75 MHz, CDCl$_3$) δ 169.3, 155.2, 143.3, 136.5, 136.4, 134.5, 133.8, 129.4, 128.8, 127.2, 126.4, 125.9, 124.4, 120.8, 119.1, 77.2, 55.4, 48.2, 42.6, 41.3, 25.1, 23.5, 21.4, 14.1. |
| 35 | 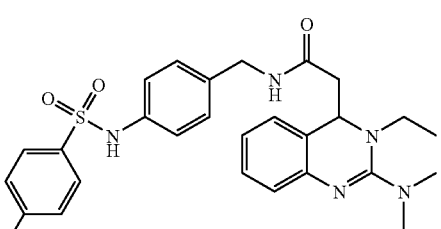 | $^1$H NMR (300 MHz, CDCl$_3$) δ 8.51(br, 1H, —CO—N<u>H</u>—CH$_2$—), 7.68(d, J=8.1 Hz, 2H, aromatic), 7.56(d, J=7.2 Hz, 1H, aromatic), 7.11-6.94(m, 9H, aromatic), 4.85(m, 1H, —CH$_2$—C<u>H</u>—N—), 4.31-4.00(m, 2H, —CO—NH—C<u>H</u>$_2$—), 3.02-3.00(m, 2H, —N—C<u>H</u>$_2$CH$_3$), 2.73(s, 6H, —NMe$_2$), 2.76(m, 1H, —CO—CH$_2$), 2.17(s, 3H, —SO$_2$—C$_4$H$_4$—C<u>H</u>$_3$), 2.00(m, 1H, —CO—CH$_2$—), 0.89(t, J=6.9 Hz, 3H, —N—CH$_2$C<u>H</u>$_3$); $^{13}$C NMR (75 MHz, CDCl$_3$) δ 169.0, 155.1, 143.0, 136.3, 134.5, 132.7, 129.2, 129.0, 128.5, 127.0, 126.0, 125.7, 124.2, 120.6, 118.5, 55.6, 47.9, 42.4, 41.2, 40.3, 21.1, 13.7. |
| 36 | 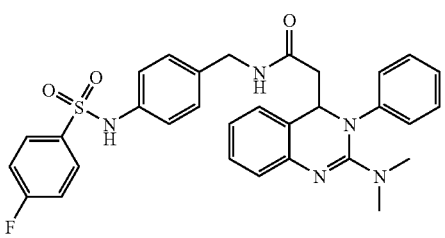 | $^1$H NMR (300 MHz, DMSO) δ 10.3(br, 1H, Ts—NH—), 8.56(t, J=5.3Hz, 1H —CO—N<u>H</u>—CH$_2$), 7.82-7.77(m, 2H, aromatic), 7.41-7.35(m, 2H, aromatic), 7.30-7.25(m, 2H, aromatic), 7.19-6.98(m, 10H, aromatic), 6.89(m, 1H, aromatic), 5.10(dd, J=3.9 and 10.5 Hz, 1H, —CH$_2$—C<u>H</u>—N—), 4.26(dd, J=5.2 and 14.5 Hz, 1H, —NH—C<u>H</u>$_2$—), 4.17(dd, J=4.8 and 14.4 Hz, 1H, —NH—C<u>H</u>$_2$), 2.66(s, 6H, —NMe$_2$), 2.55(m, 1H, —CO—CH$_2$), 2.27(dd, J=3.9 and 14.4 Hz, 1H, —CO—CH$_2$—); $^{13}$C NMR (75 MHz, DMSO) δ 169.3, 165.9, 162.6, 152.9, 145.4, 136.1, 135.9, 135.2, 129.8, 129.6, 129.3, 128.6, 127.9, 126.2, 125.0, 123.7, 121.4, 120.2, 116.6, 116.3, 60.9, 41.8, 40.9, 37.5. |

TABLE 1-continued

| Structure of No. compound | Physicochemical properties |
|---|---|
| 37 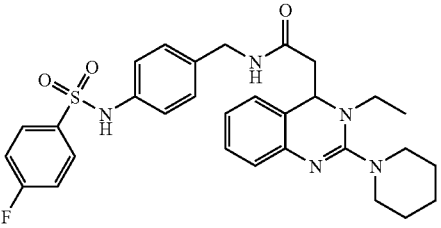 | $^1$H NMR (300 MHz, CDCl$_3$)δ 8.38(br, 1H, —CO—N$\underline{H}$—CH$_2$—), 7.89-7.84(m, 2H, aromatic), 7.56(d, J=8.4 Hz, 1H, aromatic), 7.14-7.05(m, 7H, aromatic), 7.01-6.95(m, 2H, aromatic), 4.94(dd, J=5.2 and 10.0 Hz, 1H, —CH$_2$—C$\underline{H}$—N—), 4.30(dd, J=6.3 and 14.7 Hz, 1H, —NH—C$\underline{H}_2$—), 4.23(dd, J=5.9 and 14.6 Hz, 1H, —NH—C$\underline{H}_2$—), 3.36-3.22(m, 6H, piperidinyl and —N—C$\underline{H}_2$CH$_3$), 2.67(dd, J=9.9 and 14.4 Hz, 1H, —CO—CH$_2$), 2.24(dd, J=5.1 and 14.1 Hz, 1H, —CO—CH$_2$—), 1.45(br, 6H, piperidinyl), 1.10(t, J=6.9 Hz, 3H —N—CH$_2$C$\underline{H}_3$); $^{13}$C NMR (75 MHz, CDCl$_3$) δ 169.3, 166.5, 163.1, 155.1, 136.2, 135.4, 134.8, 133.6, 129.9, 128.8, 126.5, 125.9, 124.4, 121.1, 118.9, 116.1, 55.3, 48.2, 42.6, 41.4, 25.1, 23.5, 14.0. |

Test for biological activity

In order to screen an effective T-type calcium channel blocker, the compounds prepared in the above Examples were subjected to a test for channel inhibitory effect using frog unfertilized oocytes expressing $\alpha_{1H}$ of T-type calcium channel as a primary screening method. As a result of the primary screening, the candidate compounds for blocking T-type calcium channel blockers showing 50% or more inhibitory effect were selected and subjected to the test for T-type calcium channel activity according to an electrophysiological whole cell patch clamp method. Such method uses mammalian HEK 293 cell line selectively expressing $\alpha_{1G}$ among T-type calcium channel encoding genes, wherein the $\alpha_{1G}$ is mainly expressed at nerve cells (derived from human kidney cancer cells and it was established by Prof. Edwards Ferez-Reyes of University of Virginia in Virginia, U.S.A.). The candidate compounds confirmed their T-type calcium channel blocking activities were subjected to cytotoxicity test according to 3-(4,5-dimethylthiazole-2-yl)-2,5-dimethyltetrazolium bromide (MTT) assay. As a result, it has been found that the compounds of the present invention show good inhibitory effect on the T-type calcium channel.

TEST EXAMPLE 1-1

Preparation of unfertilized Xenopus oocytes and cRNA synthesis of $\alpha_{1H}$ T-type calcium channel In order to express a gene encoding T-type calcium channel $\alpha_{1H}$ (Ca$_v$3.2) (Cribbs, L. L. et al., Circ. Res., 1998, 83, 103-109) in unfertilized Xenopus oocytes, pGEM-HEA was treated with restriction enzyme AflII to obtain a DNA fragment containing 5'-terminal region having the T-type calcium channel cDNA (AF051946). cRNA having a corresponding sequence to that of the fragment was synthesized using T7 RNA polymerase according to the manufacturer's instructions (mMESSAGE mMACHINE kit, Ambion, Austin, U.S.A.). The synthesized cRNA was quantified by measuring the O.D. value with a spectrophotometer. At this time, unfertilized oocytes were prepared from female Xenopus laevis (Xenopus I, U.S.A.) according to the following method. After the frog's abdomen was incised by about 1 cm, three to four lobes were detached therefrom with scissors and separated into small pieces to which several oocytes were attached. The small pieces were hydrolyzed in OR solution (82.5 mM NaCl, 2.5 mM KCl, 1 mM MgCl$_2$, 5 mM HEPES, pH 7.6) and supplemented with collagenase type IA (Sigma, U.S.A.) to remove defolliculation. After selecting healthy oocytes with a dissecting microscope, they were soaked in SOS solution (100 mM NaCl, 2 mM KCl, 1.8 mM CaCl$_2$, 1 mM MgCl$_2$, 5 mM HEPES, 2.5 mM pyruvate, 50 μM/ml gentamicin, pH 7.6) for 3 to 4 hours to revitalize them. 2 to 5 ng of cRNA was injected into each oocyte using Nano-injector. The oocytes were subjected to a test in order to examine the electrical properties of the channel expressed therefrom 4 to 5 days after the injection while being maintained at 18° C.

TEST EXAMPLE 1-2

Examination of Electrophysiological Property of $\alpha_{1H}$ T-type calcium channel using a two-electrode voltage clamping method The current of the calcium channel expressed from the Xenopus unfertilized oocytes was measured according to a two-electrode voltage clamping method. The current was measured in 10 mM Ba$^{2+}$ solution (10 mM Ba(OH)$_2$, 90 mM NaOH, 1 mM KCl, 0.1 mM EDTA, 5 mM HEPES, pH was adjusted to 7.4 with methanesulfonic acid). At this time, the voltage clamp and current measurement were regulated with an amplifier for unfertilized oocytes (Model OC-725C, Warner Instrument Corp., U.S.A.), and analog signals were converted into digital signals using Digidata 2000A (Analog-Digital converter, Axon Instrument). The acquisition, storage and analysis of all data were recorded in Pentium IV computer via pCLAMP8. The data were mainly collected at 5 KHz and filtered at 1 KHz (Model 902 filter; Frequency devices located at Harverhill, Mass., U.S.A.). The T-type current was generated by imposing test electric potential of −20 mV every 15 seconds on the unfertilized oocytes, the potential of which was fixed at −90 mV. A blocking percentage was calculated by comparing the potentials before and after the drug treatment. The results are shown in Table 2.

TEST EXAMPLE 2

Methods for culturing HEK 293 cells and measuring T-type calcium channel activity using an electrophysiological method HEK 293 cells were cultured in Dulbecco's modified Eagle's medium (DMEM) supplemented with 10% fetal bovine serum (FBS) and 1% penicillin/streptomycin (v/v) in 36.5° C. humidified incubator (95% air-5% CO$_2$). The culture solution was replaced with a fresh medium every 3 to 4 days and the cultured cells were subjected to sub-culture every week. At this time, the culture solution was treated with G-418 (0.5 mg/ml) solution so that only HEK 293 cells expressing $\alpha_{1G}$ T-type calcium channel can grow. The cells used for the T-type calcium channel activity assay were cultured on a cover slip coated with poly-L-lysine (0.5 mg/ml) whenever sub-cultured and their calcium channel activity was recorded 2 to 7 days after the cultivation. The current of the T-type calcium channel at a single cell level was measured according to an electrophysiological whole cell patch clamping method using EPC-9 amplifier (HEKA, German). At this time, a cell exterior solution [140 mM NaCl, 2 mM $CaCl_2$, 10 mM HEPES (pH 7.4)] and a cell interior solution [KCl 130 mM, HEPES 10 mM, EGTA 11 mM, MgATP 5 mM (pH 7.4)] were employed. The inward current caused by the T-type calcium channel activation was measured according to a T-type calcium channel protocol activated at low current. Such current occurs when the cells were converted into a whole-cell recording mode by stabbing a microglass electrode having 3-4 MΩ resistance, which was filled with the cell interior solution into a single cell and depolarized at −30 mV (50 ms duration period) every 10 seconds with fixing membrane potential to −100 mV.

TEST EXAMPLE 3

Figure 2:
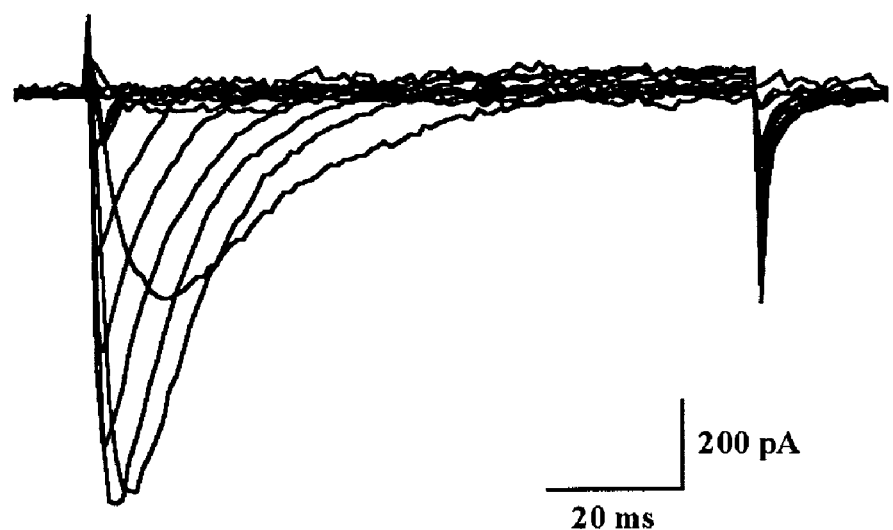
FIG. 2 is a graph showing the property of T-type calcium channel in which the activated current is quickly activated and inactivated.
Figure 3:
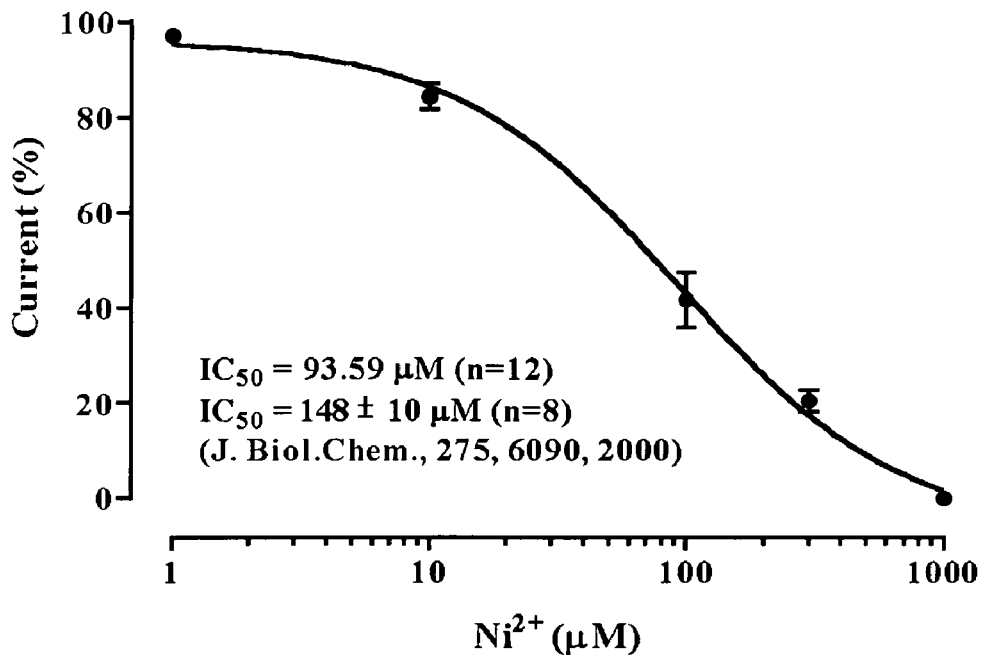
FIG. 3 is a graph showing the inhibitory effect of T-type calcium channel caused by $Ni^{2+}$.
Figure 4:
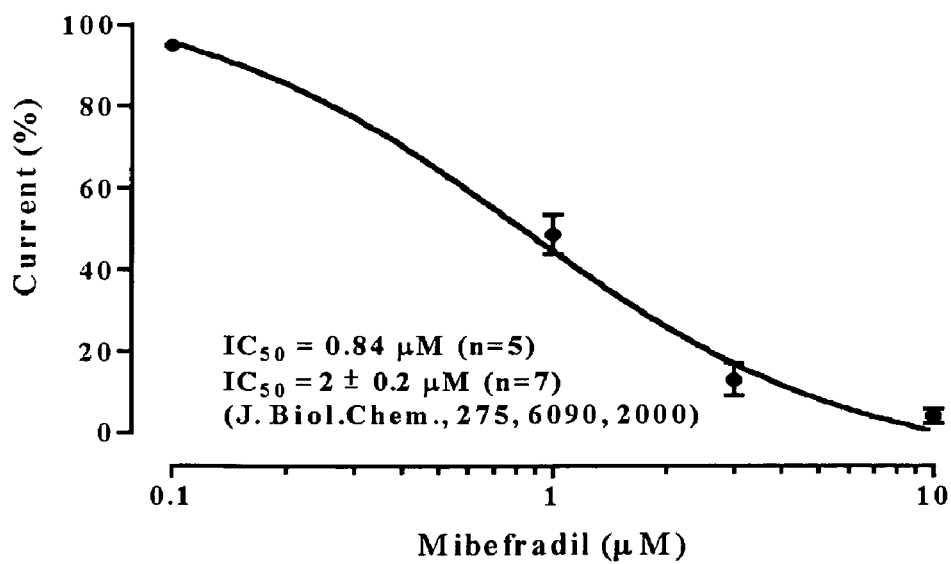
FIG. 4 is a graph showing the inhibitory effect of Mibefradil on T-type calcium channel.
Figure 5:
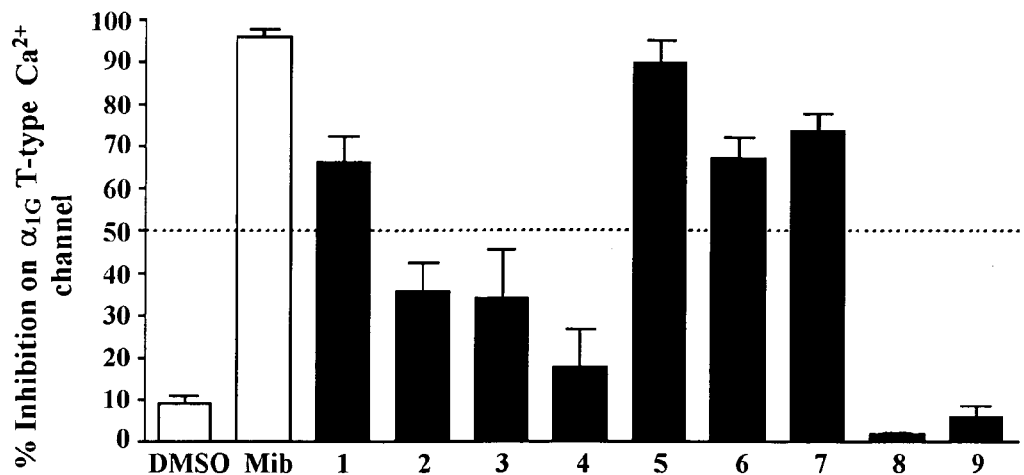
FIG. 5 is a graph showing the inhibitory effect of the compound of the present invention on T-type calcium channel.

Method for screening T-type calcium channel blockers using an electrophysiological method In order to confirm whether the cells and methods used in Test Example 2 are a suitable screening system for selecting T-type calcium channel blockers, the results obtained in Example 2 were compared with those of $\alpha_{1G}$ T-type calcium channel study reported in a public document (Monteil, A. et al., *J. Biol. Chem.* 275, 6090-6100, 2000). As can be seen in FIG. 1, it has been confirmed that since the screening system of the present invention showed 1) the maximum activation at low voltage of −30 mV (FIG. 1), 2) the fast activation-inactivation of the activated current (FIG. 2), and 3) the same $IC_{50}$ as those of $Ni^{2+}$ and Mibefradil known as T-type calcium channel blockers (FIGS. 3 and 4), it is suitable for screening T-type calcium channel blockers. Thus, the candidate compounds were subjected to a test for their inhibitory effects on the T-type calcium channel according to the screening system of the present invention, as follows. Each compound was dissolved in 100% dimethylsulfoxide (DMSO) to prepare 10 mM stock solution. The inhibitory effect on the T-type calcium channel current was examined in 10 μM sample solution (containing 0.1% DMSO) prepared by diluting the stock solution by 1000-fold. The cells were treated with each compound at a concentration of 10 μM for 30 to 60 sec with the cell exterior solution. Then, the inhibition level of peak current caused by the compound was calculated as a percentage and shown in FIG. 5.

TEST EXAMPLE 4

Analysis for cytotoxicities of T-type calcium channel blockers using MTT assay

Figure 6:
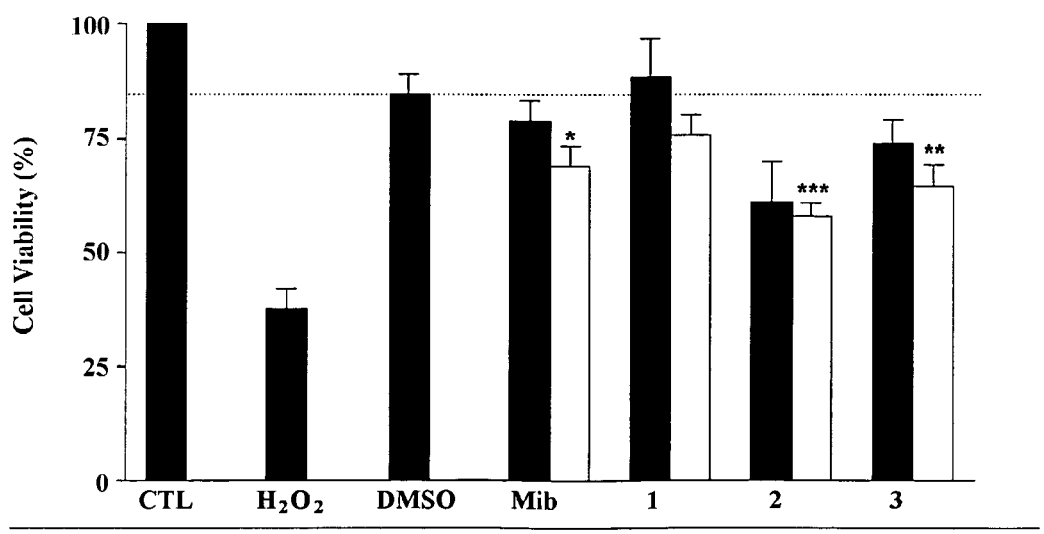
FIG. 6 is a graph showing the cytotoxicity of the compound of the present invention.

In order to analyze cytotoxicities of the T-type calcium channel blockers in HEK 293 cells, MTT assay was conducted as follows. The cultured HEK 293 cells were treated with each compound at concentrations of 10 μM and 100 μM. At this time, the cells treated with a solvent (i.e., 0.1% DMSO) were used as a negative control and the cells treated with $H_2O_2$ (125 μM) inducing cytotoxicity were used as a positive control. After 6 hours of drug treatment, the cells were treated with 50 μl of MTT (1 mg/ml) dissolved in PBS for 4 hours. Then, the reaction mixture was centrifuged to remove a supernatant and formazan crystals thus obtained were dissolved in 100 μl of DMSO. The solution's absorbance was measured at 560 nm with an automated spectrophotometric plate reader. As a result, all the compounds showing 50% or more inhibitory effect on HEK 293 cells did not show any cytotoxicity at a concentration of 10 μM and some of them showed cytotoxicity only at a high concentration (100 μM) (FIG. 6).

The results of examining the inhibitory effects of the compounds of the present invention on the T-type calcium channel in *Xenopus* unfertilized oocytes ($\alpha_{1H}$) and HEK 293 cells ($\alpha_{1G}$) are summarized in Table 2.

TABLE 2

| Compound (KIST-Code) | Formula | Xenopus oocyte (a 1H) at 100 μM | HEK293 cells (a 1G) at 10 μM ($IC_{50}$, μM) |
|---|---|---|---|
| 05001 | | 77.0 | 90.1 (0.9) |
| 05026 | | 63.8 | 40.5 (21.6) |

TABLE 2-continued

| Compound (KIST-Code) | Formula | Xenopus oocyte (a 1H) at 100 μM | HEK293 cells (a 1G) at 10 μM (IC$_{50}$, μM) |
|---|---|---|---|
| 05027 | | 20.9 | NT |
| 05028 | | 70.3 | 29.0 (35.8) |
| 05029 | | 32.7 | NT |
| 05031 | | 14.8 | NT |
| 05032 | | 14.2 | NT |

TABLE 2-continued

| Compound (KIST-Code) | Formula | Xenopus oocyte (a 1H) at 100 μM | HEK293 cells (a 1G) at 10 μM (IC$_{50}$, μM) |
|---|---|---|---|
| 05033 | | 38.9 | NT |
| 05034 | | 91.9 | 92.3 (2.5) |
| 05040 | | 66.8 | 43.5 (14.4) |
| 05041 | | 84.7 | 89.9 (0.25) |
| 05042 | | 80.5 | 89.0 (0.20) |
| mibefradil | | 86.0 | 95.9 (0.84) |

The calcium channel inhibitory effect of Mibefradil, which is used as a control, was measured according to the activity screening method of the present invention. As shown in Table 2, Mibefradil showed 86% of inhibitory effect (100 µM) on the *Xenopus* fertilized oocytes ($\alpha_{1H}$) and 95.9% of inhibitory effect (10 µM, $IC_{50}$=0.84 µM) on HEK 293 cells ($\alpha_{1G}$). Meanwhile, KYS05001, which is one of the compounds of the present invention, showed 77% of inhibitory effect (100 µM) on the *Xenopus* cytes ($\alpha_{1H}$) and 90.1% of inhibitory effect (10 µM, $IC_{50}$=0.9 µM) on HEK 293 cells ($\alpha_{1G}$). Further, KYS05041 and KYS05042 showed 84.7% and 80.5% of inhibitory effects (100 µM) on the *Xenopus* fertilized oocytes (α1H) and 89.9% and 89.0% of inhibitory effects (10 µM) on HEK 293 cells ($\alpha_{1G}$), respectively. Their $IC_{50}$ values were 0.25 µM and 0.20 µM, respectively. Accordingly, when comparing the $IC_{50}$ values, KYS05001 showed almost the same calcium channel inhibitory effect as Mibefradil, while KYS05041 and KYS05042 showed about 3.4 and 4.2-fold higher channel inhibitory effect than Mibefradil, respectively.

TEST EXAMPLE 5

Confirmation of selectivity of the compound for other ion channels

In order to examine the selectivity of the compound of the present invention for other ion channels, the inhibitory effects of KYS05001, KYS05041 and KYS05042 on $Na^{2+}$ channel and high voltage-activated Ca2+ channel (HVA) were measured according to a conventional method (Lee, J.-H. et al., *J. Neurophysiol.* 2002, 87, 2844-2850) using MPG (major pelvic ganglion).

Male Sprague-Dawley rats having about 250 g of an average body weight were employed as experimental animals. After the rats were anesthetized with sodium pentobarbital (50 mg/kg, i.p.), the abdomen was cut open immediately. MPG located on the left side of the prostate was extracted and then transferred in cold (4° C.) Hank's balanced salt solution (HBSS, GibcoBRL). The connective tissue encompassing the ganglion was stripped therefrom and a small gap was made carefully on the naked ganglion with a sharp knife. Then, the ganglion was cultured in 10 ml of modified Earle's balanced salt solution (EBSS, pH 7.4, GibcoBRL) supplemented with 0.7 mg/ml of collagenase (type D), 0.3 mg/ml of trypsin and 0.1 mg/ml of DNAse type I at 35° C. for 1 hour (Zhu et al., *J. Physiol. Lond.* 1995, 489, 363-375). At this time, 3.6 g/l of glucose and 10 mM HEPES were added to EBSS. After the cultivation was completed, the culture flask was shaken to separate call clusters into a single nerve cell and subjected to centrifugation at 1000 rpm with a clinical centrifuge (International Equipment Company, Mass., U.S.A.). The separated single nerve cells were re-suspended in MEM (GibcoBRL) supplemented with 10% fetal bovine serum, 1% glutamine and 1% penicillin/streptomycin. They were then spread on a polystyrene culture dish (35 mm) coated with poly-L-lysine. The culture dish was incubated at 37° C. humidified incubator (95% air-5% $CO_2$) and the cells were used in the following experiment within 24 hours after the separation.

The voltage-dependent calcium and sodium current were recorded according to a typical patch clamping method using a patch clamp amplifier (Axopatch 1D, Axon Instruments, Foster City, Calif., U.S.A.) at a whole-cell ruptured configuration (Hamill et al., *Pflügers Arch.* 1981, 391, 85-100). An electrode was made from a borosilicate glass capillary tube (outer diameter; 1.65 mm, inner diameter; 1.2 mm, Corning 7052, Garner Glass Co., Claremont, Calif., U.S.A.) using P-97 Flaming-Brown micropipette puller (Sutter Instrument Co., Novato, Calif., U.S.A.) and forged smoothly by heating with a microforge. The electrode showing 1~3 MΩ of resistance when filled with a solution was used for the following experiment. The culture dish containing the nerve cells was placed on an inverted microscope and the cell exterior solution was flowed into the dish at a flow rate of about 1~2 ml/min. The membrane capacitance and series resistance were corrected by 80% or more with an amplifier. The voltage generation and record of calcium current were carried out using S4 software (provided by Dr. Stephen R. Ikeda, National Institute on Alcohol Abuse and Alcoholism, NIH, USA) equipped in Macintosh computer, which was connected to an analogue/digital converter (Digidata 1200, Axon Instruments Co.). The calcium current, which passed through a low band pass filter at 2~5 kHz, was stored in Macintosh computer and analyzed with IGOR PRO (Wave-Metrics, Lake Oswego, Oreg., U.S.A.). All the experiments were conducted at a room temperature ranging from 20 to 22° C.

The electrode for measuring the calcium current was filled with the solution comprising 120 mM N-methyl-D-glucamine (NMG) methanesulfonate (MS), 20 mM tetraethylammonium (TEA)-MS, 20 mM HCl, 11 mM EGTA, 10 mM HEPES, 1 mM $CaCl_2$, 4 mM MgATP, 0.3 mM $Na_2GTP$ and 14 mM tris-phosphocreatine (pH 7.2, 290 mOsm). The extracellular infusion fluid was composed of 140 mM MS, 145 mM TEA-OH, 10 mM HEPES, 15 mM glucose, 10 mM $CaCl_2$ and 0.0003 mM tetrodotoxin (TTX, pH 7.4, 320 mOsm). The electrode for measuring the sodium current was filled with the solution comprising 30 mM NaCl, 140 mM NMG-MS, 11 mM EGTA, 10 mM HEPES, 1 mM $CaCl_2$, 4 mM MgATP and 0.3 mM $Na_2GTP$ (pH 7.2, 290 mOsm). The extracellular infusion fluid was composed of 50 mM NaCl, 90 mM TEACl, 10 mM HEPES, 15 mM glucose, 10 mM $CaCl_2$ and 10 mM $MgCl_2$ (pH 7.4, 320 mOsm).

The results are summarized in Table 3.

TABLE 3

Inhibitory effect of the compound of the present invention on other ion channels (MPG neuron; concentration of 10 µM)

| | $Ca^{2+}$ channel[a] | | |
|---|---|---|---|
| | T-type (LVA) | N-type (HVA) | $Na^+$ channel[a] |
| KYS05001 | 90.1% | n.i.[b] | n.i.[b] |
| KYS05041 | 89.9% | >89% | n.i.[b] |
| KYS05042 | 89.0% | >90% | n.i.[b] |

[a]Lee, J. H. et al., J. Neurophysiol. 2002, 87, 2844-2850;
[b]n.i. = no inhibitory effect As can be seen in Table 3, KYS05001, KYS05041 and KYS05042 showed higher selectivity for the calcium channel than the sodium channel. Further, in case of examining the selectivity for the sub-types of the calcium channel, KYS05041 and KYS05042 showed relatively lower selectivity. This is because it inhibited both the T-type (LVA) and N-type (HVA) calcium channels. However, KYS05001 showed higher selectivity and selectively inhibited only the T-type (LVA) calcium channel.

What is claimed is:

1. A 3,4-dihydroquinazoline derivative of Formula 1 or a salt thereof:

<Formula 1>

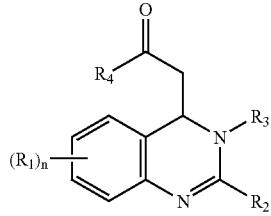

wherein, n is an integer ranging from 1 to 4;
$R_1$ is hydrogen;
$R_2$ is $C_1$-$C_6$ alkyl; phenyl; 4-morpholinyl; piperazinyl having a $C_1$-$C_4$ alkyl substituent at the $4^{th}$ position; 1-pyrrolidinyl; 1-piperidinyl; or —$NR_6R_7$, wherein $R_6$ and $R_7$ are each independently $C_1$-$C_6$ alkyl;
$R_3$ is $C_1$-$C_6$ alkyl or phenyl;

$R_4$ is

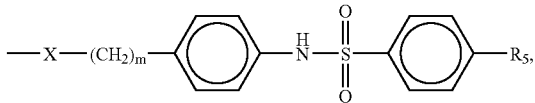

wherein X is O or NH; m is an integer ranging from 1 to 4; and
$R_5$ is methyl or F.

2. The 3,4-dihydroquinazoline derivative of claim 1 or the salt thereof, which is 4-{N-[4-(4-methylbenzenesulfonylamido)benzyl]acetamido}-3-phenyl-2-(piperidine-1-yl)-3,4-dihydroquinazoline.

3. The 3,4-dihydroquinazoline derivative of claim 1 or the salt thereof, which is 4-{N-[4-(4-fluorobenzenesulfonylamido)benzyl]acetamido}-3-phenyl-2-(piperidine-1-yl)-3,4-dihydroquinazoline.

* * * * *